(12) United States Patent
Nicholas

(10) Patent No.: US 11,801,050 B2
(45) Date of Patent: Oct. 31, 2023

(54) HAND-HELD SURGICAL INSTRUMENTS

(71) Applicant: Covidien LP, Mansfield, MA (US)

(72) Inventor: David A. Nicholas, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 99 days.

(21) Appl. No.: 17/471,416

(22) Filed: Sep. 10, 2021

(65) Prior Publication Data

US 2022/0104809 A1 Apr. 7, 2022

Related U.S. Application Data

(60) Provisional application No. 63/087,970, filed on Oct. 6, 2020.

(51) Int. Cl.
*A61B 17/00* (2006.01)
*A61B 17/068* (2006.01)
*A61B 90/00* (2016.01)

(52) U.S. Cl.
CPC .......... *A61B 17/0686* (2013.01); *A61B 90/08* (2016.02); *A61B 2017/0046* (2013.01); *A61B 2017/00367* (2013.01); *A61B 2090/0811* (2016.02)

(58) Field of Classification Search
CPC ........... A61B 2017/00367; A61B 2017/00389; A61B 17/068
See application file for complete search history.

(56) References Cited

U.S. PATENT DOCUMENTS

| | | | |
|---|---|---|---|
| 4,196,348 A | 4/1980 | Iwakiri et al. | |
| 4,803,362 A | 2/1989 | Butts | |
| 5,312,023 A * | 5/1994 | Green | A61B 17/07207 227/19 |
| 5,321,311 A | 6/1994 | Umemura et al. | |
| 5,564,615 A * | 10/1996 | Bishop | A61B 17/0682 227/19 |
| 5,747,953 A | 5/1998 | Philipp | |
| 5,865,361 A * | 2/1999 | Milliman | A61B 17/068 227/176.1 |
| 6,013,991 A | 1/2000 | Philipp | |

(Continued)

FOREIGN PATENT DOCUMENTS

| | | |
|---|---|---|
| CN | 101227187 A | 7/2008 |
| CN | 203014768 U | 6/2013 |

(Continued)

OTHER PUBLICATIONS

European Search Report dated Mar. 2, 2022, issued in corresponding EP Appln. No. 21200913, 8 pages.

*Primary Examiner* — Gloria R Weeks
(74) *Attorney, Agent, or Firm* — CARTER, DELUCA & FARRELL LLP

(57) ABSTRACT

A hand-held surgical instrument includes a handle housing and a shaft assembly extending distally from the handle housing. The shaft assembly includes an elongate body configured to translate from a distal position to a proximal position in response to an insertion of a surgical loading unit into a distal end portion of the shaft assembly. The shaft assembly has a cam plate configured to convert rotational motion into an articulation of an end effector of the surgical loading unit. When the elongate body is in the distal position, the elongate body is configured to prevent rotation of the cam plate.

19 Claims, 14 Drawing Sheets

(56) References Cited

U.S. PATENT DOCUMENTS

| | | | |
|---|---|---|---|
| 6,025,683 A | 2/2000 | Philipp | |
| 6,517,565 B1 | 2/2003 | Whitman et al. | |
| 6,786,382 B1* | 9/2004 | Hoffman | A61B 17/07207 |
| | | | 227/180.1 |
| 6,960,894 B2 | 11/2005 | Carusillo et al. | |
| 7,638,958 B2 | 12/2009 | Philipp et al. | |
| 8,033,442 B2* | 10/2011 | Racenet | A61B 17/068 |
| | | | 227/181.1 |
| 8,061,576 B2* | 11/2011 | Cappola | A61B 17/0682 |
| | | | 227/176.1 |
| 8,480,703 B2* | 7/2013 | Nicholas | A61B 17/07207 |
| | | | 606/205 |
| 8,968,276 B2 | 3/2015 | Zemlok et al. | |
| 9,307,986 B2 | 4/2016 | Hall et al. | |
| 9,326,767 B2 | 5/2016 | Koch, Jr. et al. | |
| 9,398,911 B2 | 7/2016 | Auld | |
| 9,468,436 B2 | 10/2016 | Groiso | |
| 9,554,794 B2 | 1/2017 | Baber | |
| 9,597,104 B2 | 3/2017 | Nicholas et al. | |
| 9,654,050 B2 | 5/2017 | Kokinelis | |
| 9,693,774 B2* | 7/2017 | Gettinger | A61B 17/07292 |
| 9,700,309 B2 | 7/2017 | Jaworek | |
| 9,700,318 B2 | 7/2017 | Scirica et al. | |
| 9,775,610 B2 | 10/2017 | Nicholas et al. | |
| 9,782,169 B2 | 10/2017 | Kimsey | |
| 9,782,187 B2 | 10/2017 | Zergiebel | |
| 9,801,646 B2 | 10/2017 | Zergiebel | |
| 9,991,069 B2 | 6/2018 | Nicholas et al. | |
| 10,245,030 B2* | 4/2019 | Hunter | A61B 17/068 |
| 11,076,850 B2* | 8/2021 | Whitfield | A61B 17/068 |
| 2008/0035701 A1* | 2/2008 | Racenet | A61B 17/07207 |
| | | | 227/176.1 |
| 2008/0083811 A1* | 4/2008 | Marczyk | A61B 17/068 |
| | | | 227/176.1 |
| 2009/0095790 A1 | 4/2009 | Whitman et al. | |
| 2009/0206124 A1* | 8/2009 | Hall | A61B 17/068 |
| | | | 227/175.1 |
| 2010/0038403 A1 | 2/2010 | D'Arcangelo | |
| 2010/0171026 A1 | 7/2010 | Saitou et al. | |
| 2011/0121049 A1 | 5/2011 | Malinouskas et al. | |
| 2011/0204119 A1 | 8/2011 | McCuen | |
| 2012/0089131 A1 | 4/2012 | Zemlok et al. | |
| 2012/0130420 A1 | 5/2012 | Nicholas | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2012/0298720 A1 | 11/2012 | Marczyk | |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2015/0235789 A1 | 8/2015 | Calderoni | |
| 2015/0374372 A1 | 12/2015 | Zergiebel et al. | |
| 2017/0245654 A1 | 8/2017 | Cutler | |
| 2019/0038283 A1 | 2/2019 | Shelton, IV et al. | |

FOREIGN PATENT DOCUMENTS

| | | |
|---|---|---|
| EP | 2055243 A2 | 5/2009 |
| EP | 2090251 A2 | 8/2009 |
| EP | 2455007 A2 | 5/2012 |
| EP | 2777539 A2 | 9/2014 |
| EP | 3011910 A1 | 4/2016 |
| KR | 20020020332 A | 3/2002 |
| KR | 20070000199 U | 2/2007 |
| WO | 2008146415 A1 | 12/2008 |
| WO | 2017123837 A2 | 7/2017 |

* cited by examiner

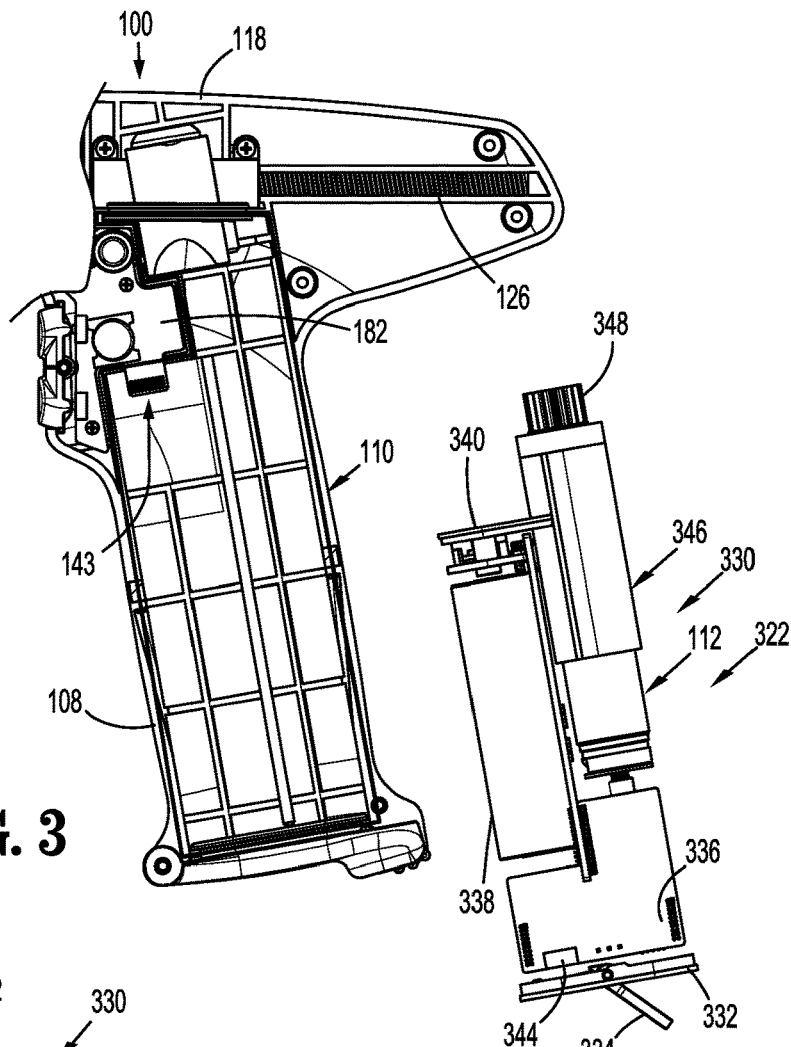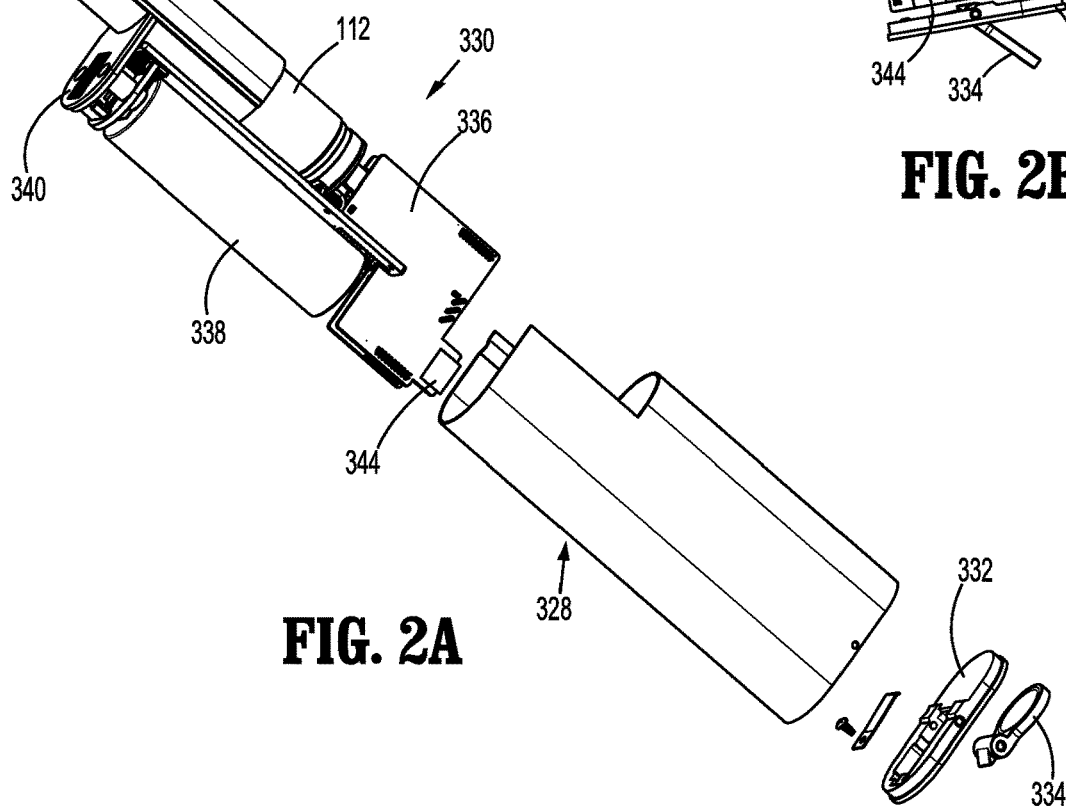
FIG. 3
FIG. 2B
FIG. 2A

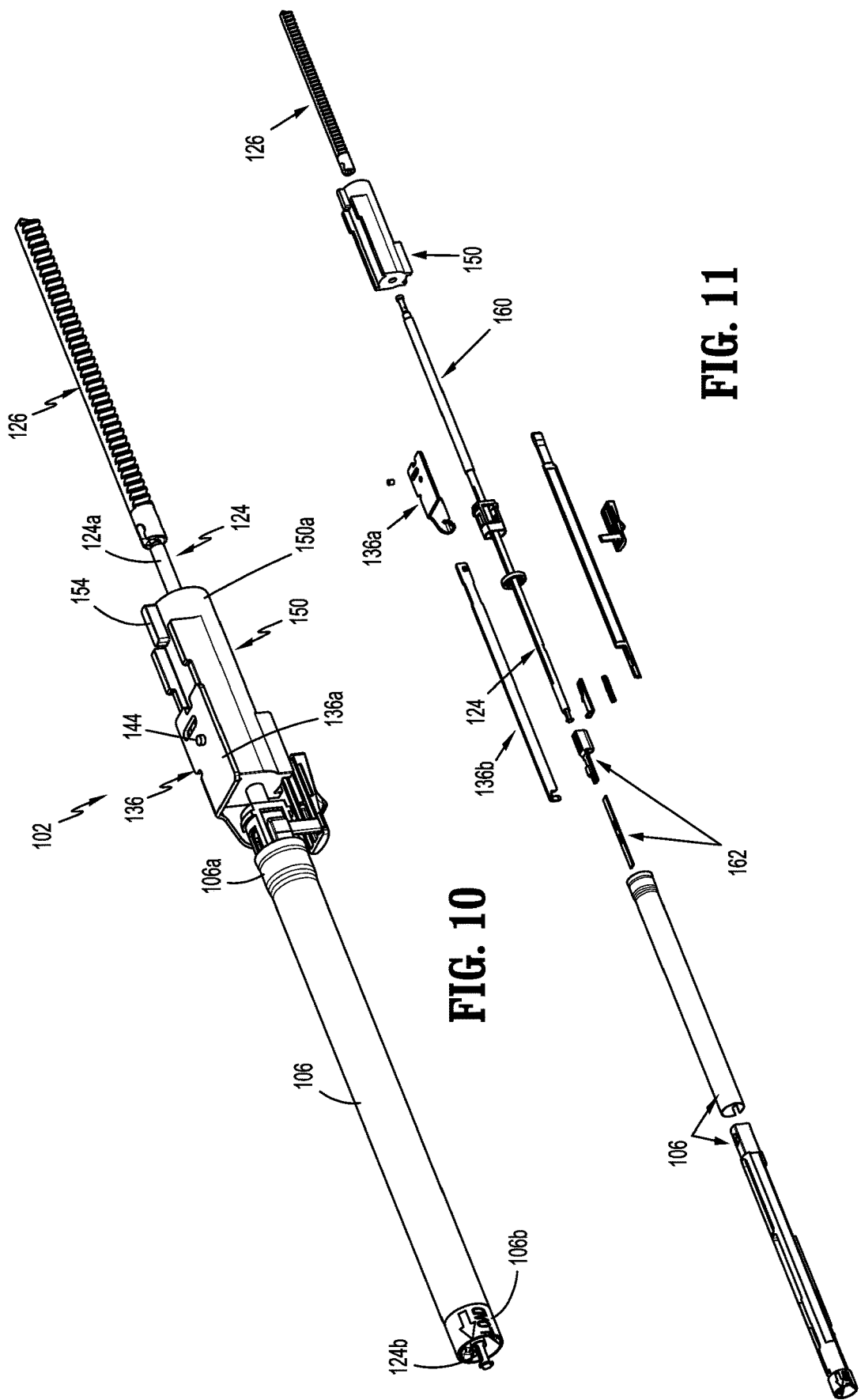

HAND-HELD SURGICAL INSTRUMENTS

CROSS-REFERENCE TO RELATED APPLICATIONS

This application claims the benefit of and priority to U.S. Provisional Patent Application No. 63/087,970, filed Oct. 6, 2020, the entire contents of which are being incorporated by reference herein.

This application is related to U.S. patent application Ser. No. 17/090,093, filed Nov. 5, 2020 and U.S. patent application Ser. No. 17/089,789, filed Nov. 5, 2020, the entire contents of each of which are being incorporated by reference herein.

BACKGROUND

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

SUMMARY

In one aspect of the present disclosure, a hand-held surgical instrument is provided and includes a handle assembly, a shaft portion having a proximal end portion and a distal end portion, a knob housing coupled between the proximal end portion of the shaft portion and the handle assembly, an articulation lever rotationally coupled to the knob housing, a cam plate non-rotationally coupled to the articulation lever and disposed within the knob housing, a slider supported in the knob housing and configured to translate within and relative to the knob housing between a proximal position and a distal position, and a surgical loading unit having a proximal body portion and an end effector pivotably coupled to the proximal body portion. The cam plate defines a notch therein and the slider has a tab configured for receipt in the notch of the cam plate when the slider is in the distal position to prevent rotation of the cam plate. The proximal body portion of the surgical loading unit is configured to detachably couple to the distal end portion of the shaft portion. The cam plate is configured to operably couple to the end effector such that the end effector articulates relative to the proximal body portion in response to a rotation of the cam plate. The surgical loading unit is configured to move the slider toward the proximal position upon assembling the surgical loading unit to the distal end portion of the shaft portion.

In aspects, the hand-held surgical instrument may further include a flag and a sensor disposed adjacent the flag. The flag may be attached to the slider and configured to move with the slider between the proximal and distal positions. The sensor may be configured to sense whether the slider is in the proximal position or the distal position.

In aspects, the sensor may be a photointerrupter fixed within the handle assembly, and the flag may be configured to block a signal of the photointerrupter when the slider is in the proximal position.

In aspects, the hand-held surgical instrument may further include a motor configured to actuate a function of the end effector. The sensor may be in communication with the motor and configured to prevent operation of the motor when the sensor senses that the slider is in the distal position and/or permit operation of the motor when the sensor senses that the slider is in the proximal position.

In aspects, the slider may be an elongate body resiliently biased toward the distal position.

In aspects, the hand-held surgical instrument may further include an articulation link extending through the shaft portion. The articulation link may include a proximal end portion having a cam pin, and a distal end portion configured to operably couple to the end effector. The cam plate may define a cam slot in which the cam pin is received. The articulation link may be configured to translate in response to a rotation of the cam plate to articulate the end effector relative to the proximal body portion.

In aspects, the hand-held surgical instrument may further include a pawl received in the knob housing. The cam plate may have a plurality of teeth extending from an outer periphery of the cam plate. The pawl may be engaged to the plurality of teeth to maintain a radial orientation of the cam plate.

In aspects, the shaft portion may be configured to rotate about a longitudinal axis defined by the shaft portion in response to a manual rotation of the knob housing.

In aspects, the hand-held surgical instrument may further include a firing rod extending longitudinally through a longitudinal passageway defined through the slider. The firing rod may have a distal end portion configured to detachably couple to the surgical loading unit. The firing rod may be configured to translate through the shaft portion to actuate a function of the end effector.

In accordance with another aspect of the disclosure, a hand-held surgical instrument is provided and includes a handle housing, a shaft portion extending distally relative to the handle housing, a knob housing disposed between a proximal end portion of the shaft portion and the handle housing, an elongate body supported in the knob housing, and a cam plate configured to convert rotational motion into an articulation of an end effector of the surgical loading unit. The elongate body is configured to translate from a distal position to a proximal position in response to an insertion of a surgical loading unit into a distal end portion of the shaft portion. The elongate body has a tab, and the cam plate defines a notch therein configured for receipt of the tab of the elongate body when the elongate body is in the distal position to prevent rotation of the cam plate.

In aspects, the hand-held surgical instrument may further include the surgical loading unit, which may include a proximal body portion configured to detachably couple to the distal end portion of the shaft portion, and the end effector. The end effector may be pivotably coupled to the proximal body portion. The cam plate may be configured to operably couple to the end effector such that the end effector articulates relative to the proximal body portion in response to a rotation of the cam plate.

In aspects, the hand-held surgical instrument may further include a flag attached to the elongate body and a sensor disposed adjacent the flag. The flag may be configured to move with the elongate body between the proximal and distal positions. The sensor may be configured to sense whether the elongate body is in the proximal position, thereby indicating the surgical loading unit is assembled to the hand-held surgical instrument.

In aspects, the sensor may be a photointerrupter, and the flag may be configured to block a signal of the photointerrupter when the elongate body is in the proximal position.

In aspects, the hand-held surgical instrument may further include a motor configured to actuate a function of the surgical loading unit. The sensor may be in communication with the motor and configured to permit operation of the motor when the sensor senses that the elongate body is in the proximal position.

In aspects, the elongate body may be resiliently biased toward the distal position.

In aspects, the hand-held surgical instrument may further include an articulation lever and an articulation link. The articulation lever may be rotationally coupled to the knob housing and non-rotationally coupled to the cam plate. The articulation link may include a proximal end portion having a cam pin, and a distal end portion configured to operably couple to the surgical loading unit. The cam plate may define a cam slot in which the cam pin is received. The articulation link may be configured to translate in response to a rotation of the cam plate by the articulation lever.

In aspects, the hand-held surgical instrument may further include a firing rod extending longitudinally through a longitudinal passageway defined through the elongate body. The firing rod may have a distal end portion configured to detachably couple to the surgical loading unit and configured to translate through the shaft portion to actuate a function of the surgical loading unit.

In aspects, the hand-held surgical instrument may further include a tubular shaft disposed about the firing rod. The tubular shaft may have a proximal end portion engaged to the elongate body, and a distal end portion configured to be engaged by the surgical loading unit such that the tubular shaft translates the elongate body from the distal position to the proximal position upon receipt of the surgical loading unit in the distal end portion of the shaft portion.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIG. 2A is a perspective view, with parts separated, illustrating a surgical instrument module of the handle assembly of FIG. 1 including a power assembly and an outer shell;

FIG. 2B is an assembled front view illustrating the power assembly of the instrument module of FIG. 2A;

FIG. 3 is a side view, with a housing half of the handle housing removed, illustrating internal components of the handle assembly;

FIG. 10 is a side perspective view illustrating the shaft assembly of FIG. 9;

FIG. 11 is a perspective view, with parts separated, of the shaft assembly of FIG. 10;

DETAILED DESCRIPTION

Figure 1:
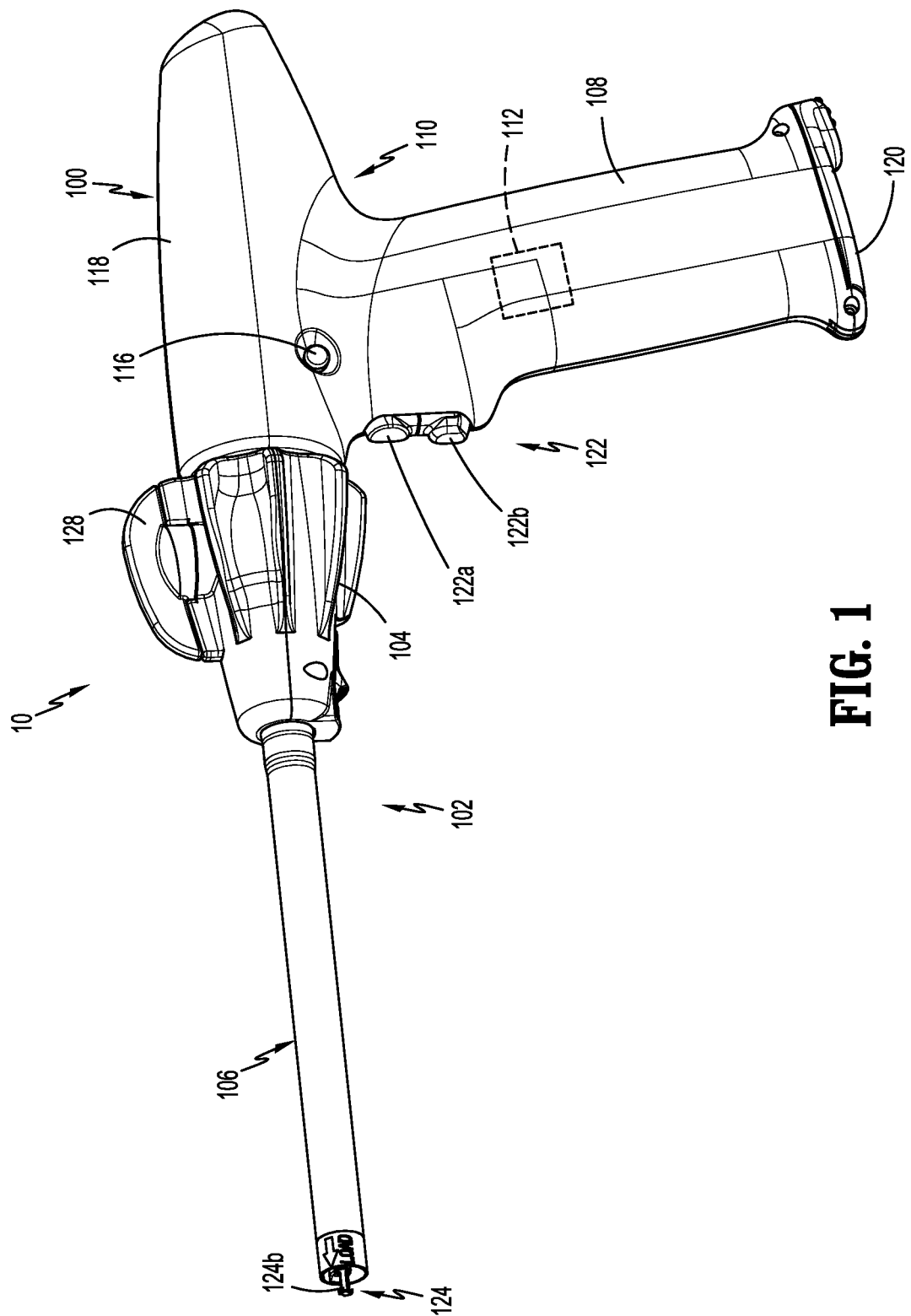
FIG. 1 is a side perspective view illustrating a hand-held electromechanical surgical instrument including a handle assembly and a shaft assembly coupled to the handle assembly.

Embodiments of the presently disclosed hand-held surgical stapling instruments are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

As will be described in detail below, provided is a hand-held surgical instrument including a handle assembly, a shaft assembly coupled to the handle assembly, and a surgical loading unit detachably coupled to a distal end of the shaft assembly. The shaft assembly has a motor-driven firing rod configured to carry out a function of a surgical end effector of the surgical loading unit. The shaft assembly has a manual articulation lever operably coupled to the end effector for manually articulating the end effector between a non-articulation orientation and various articulated orientations. The shaft assembly includes a cam plate that is rotated by the articulation lever, and a slider block that translates proximally during loading of the surgical loading unit into the shaft assembly. The slider block interlocks with the cam plate when no surgical loading unit is assembled to the shaft assembly, whereby the slider block prevents manual rotation of the articulation lever. As such, articulation is not permitted unless a surgical loading unit is properly engaged to the shaft assembly. Other features and benefits of the disclosed surgical instruments are further detailed below.

Figure 17:
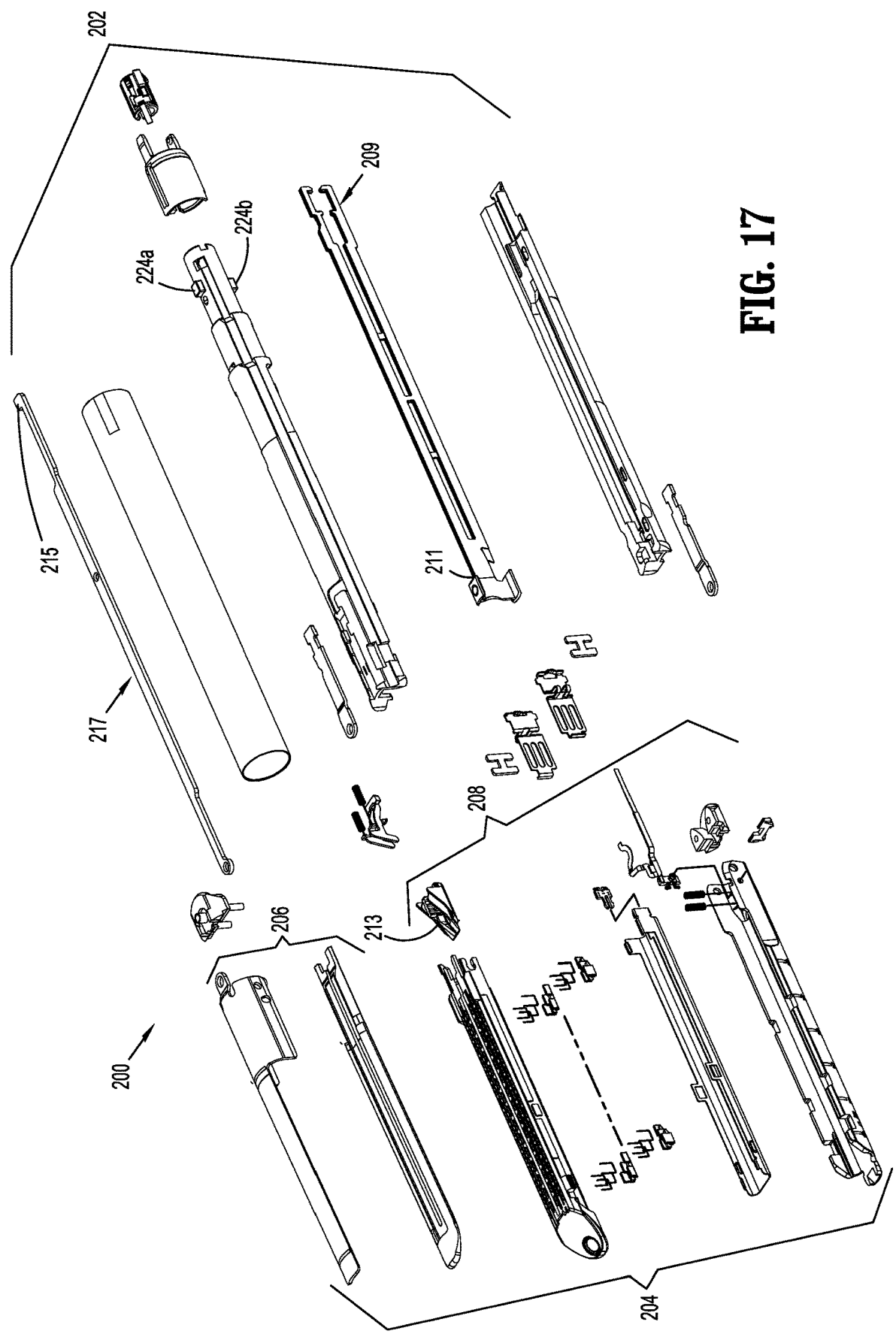
FIG. 17 is a perspective view, with parts separated, illustrating details of a surgical loading unit.
Figure 18:
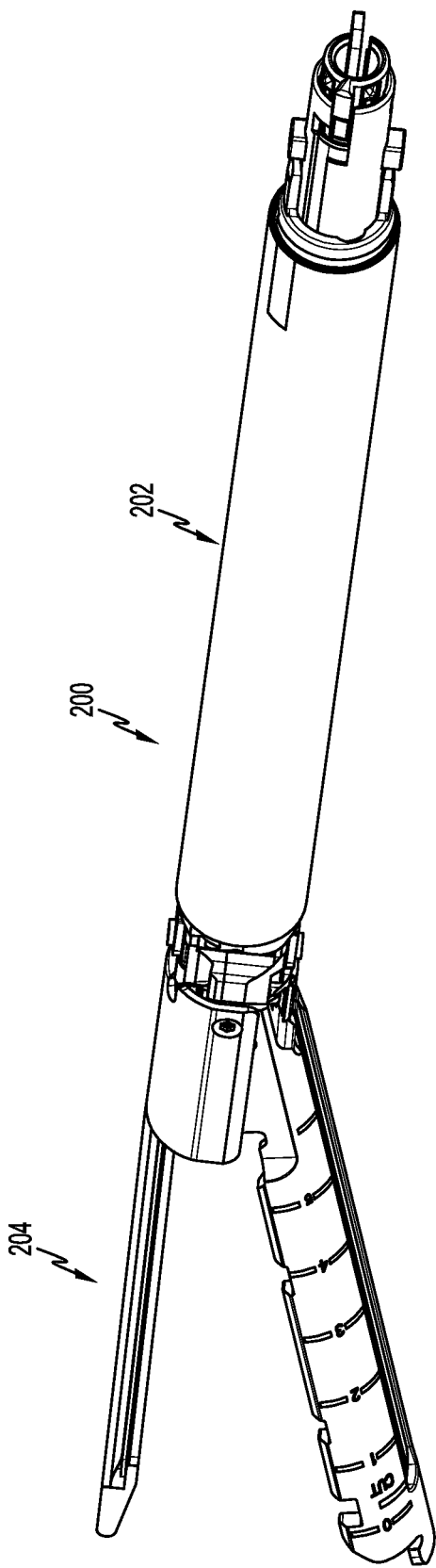
FIG. 18 is a perspective view illustrating the surgical loading unit of FIG. 17.
Figure 19:
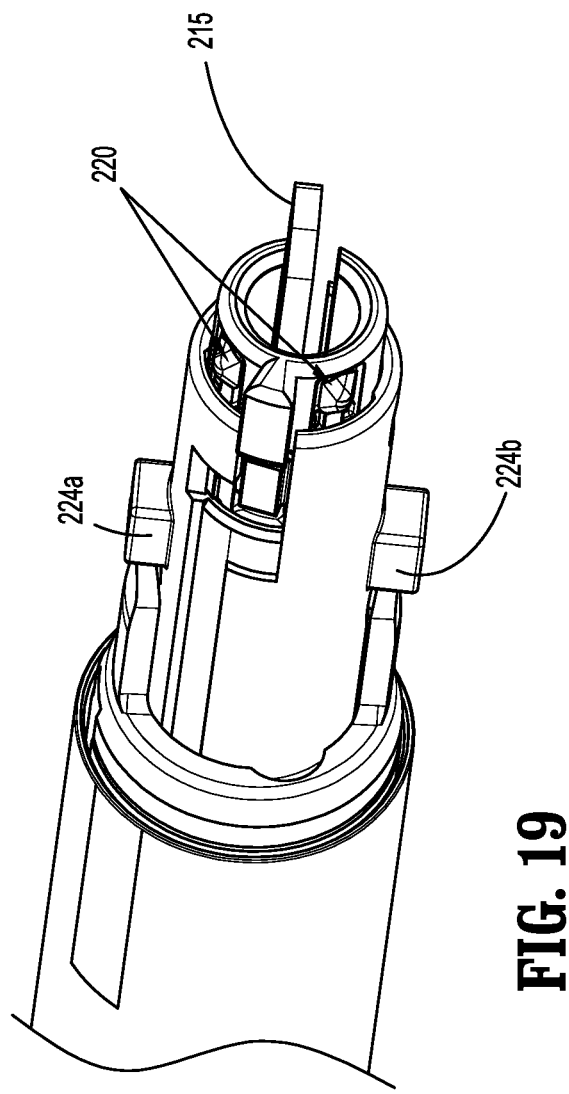
FIG. 19 is an enlarged perspective view illustrating a proximal end of the surgical loading unit of FIG. 18.

With reference to FIG. 1, a surgical instrument, in accordance with an embodiment of the present disclosure, is generally designated as 10, and is in the form of a powered hand-held electromechanical surgical instrument configured for selective coupling thereto of a plurality of different surgical loading units, for example, the surgical loading unit 200 of FIGS. 17-19. As will be described in further detail below, the surgical loading unit 200 includes a proximal body portion 202 detachably coupled to a shaft assembly 102 of the surgical instrument 10, and an end effector 204 pivotably coupled to the proximal body portion 202. The end effector 204 is configured for actuation and manipulation by the powered hand-held electromechanical surgical instrument 10.

The hand-held electromechanical surgical instrument 10 includes a handle assembly 100 and the shaft assembly 102, which includes a knob housing 104 coupled to the handle assembly 100, and a shaft portion 106 extending distally from the knob housing 104 and configured for selective connection with a surgical attachment, such as, for example, the surgical loading unit 200. The handle assembly 100 includes a disposable and sterile handle housing 110 and an instrument module 322 (FIGS. 2A-2B) configured for removable receipt within handle housing 110.

The handle housing 110 has a body, such as, for example, a barrel portion 118, a handle portion 108 extending perpendicularly downward from the barrel portion 118 or transversely and proximally from the barrel portion 118, and a hinged door 120 pivotably coupled to the handle portion 108. The door 120 is selectively opened and closed to allow for the insertion or removal of the instrument module 322. The handle portion 108 and the door 120 each have an inner periphery collectively defining a sterile barrier for the instrument module 322 upon closing the door 120. In aspects, a proximal end portion or any suitable location of the barrel portion 118 may have a clear window (not shown) to allow for viewing of a display (e.g., an LCD, not shown).

The handle assembly 100 has a fire switch 122 configured and adapted to actuate the various functions of the end effector 200. The fire switch 122 may be constructed as a toggle bar pivotably coupled to the handle portion 108 of the handle housing 110. An activation of the fire switch 122 activates a motor 112 to advance or retract a firing rod 124 of the shaft assembly 102 depending on whether a top button 122a or a bottom button 122b of the fire switch 122 is actuated. The firing rod 124 has a distal end portion 124b configured to couple to a drive assembly 209 (FIG. 17) of the surgical loading unit 200 (which includes a knife rod 211 and an actuation sled 213), such that advancement of the firing rod 124 advances the drive assembly 209 of the surgical loading unit 200, which closes the jaw members 206, 208 of the end effector 200 and fires the end effector 200 when a safety switch 116 is in an actuated state.

With reference to FIGS. 2A, 2B, and 3, the surgical instrument module 322 of the handle assembly 100 is configured for powering surgical instrument 10. In other aspects, other means for powering surgical instrument 10 are contemplated, such as, for example, a battery-powered motor that is permanently fixed within handle housing 110. The surgical instrument module 322 includes a sterile outer shell 328 and a reusable power assembly 330 configured for removably receipt in the outer shell 328. The outer shell 328 has a cover 332 received in an open bottom end of the outer shell 328, and a spring-loaded pull tab 334 to facilitate removal of the cover 332.

The power assembly 330 of the instrument module 322 includes the motor 112, such as, for example, an electrical drive motor, which is electrically connected or wirelessly connected to a printed circuit board 336 and a battery 338. In aspects, the battery 338 may include a boost circuit and may be rechargeable (e.g., wirelessly). The battery 338 has a card edge connector 340 configured for detachable receipt of a card edge header 143 of the handle assembly 100 to allow for communication from the fire switch 106, the safety switch 116, and an articulation encoder to the battery 338. The printed circuit board 336 may include a USB charging connector 344 to allow for the battery 338 to be recharged with a USB charger or wirelessly (e.g., via induction). In aspects, the printed circuit board 336 may have a motor controller or a processor.

Figure 4:
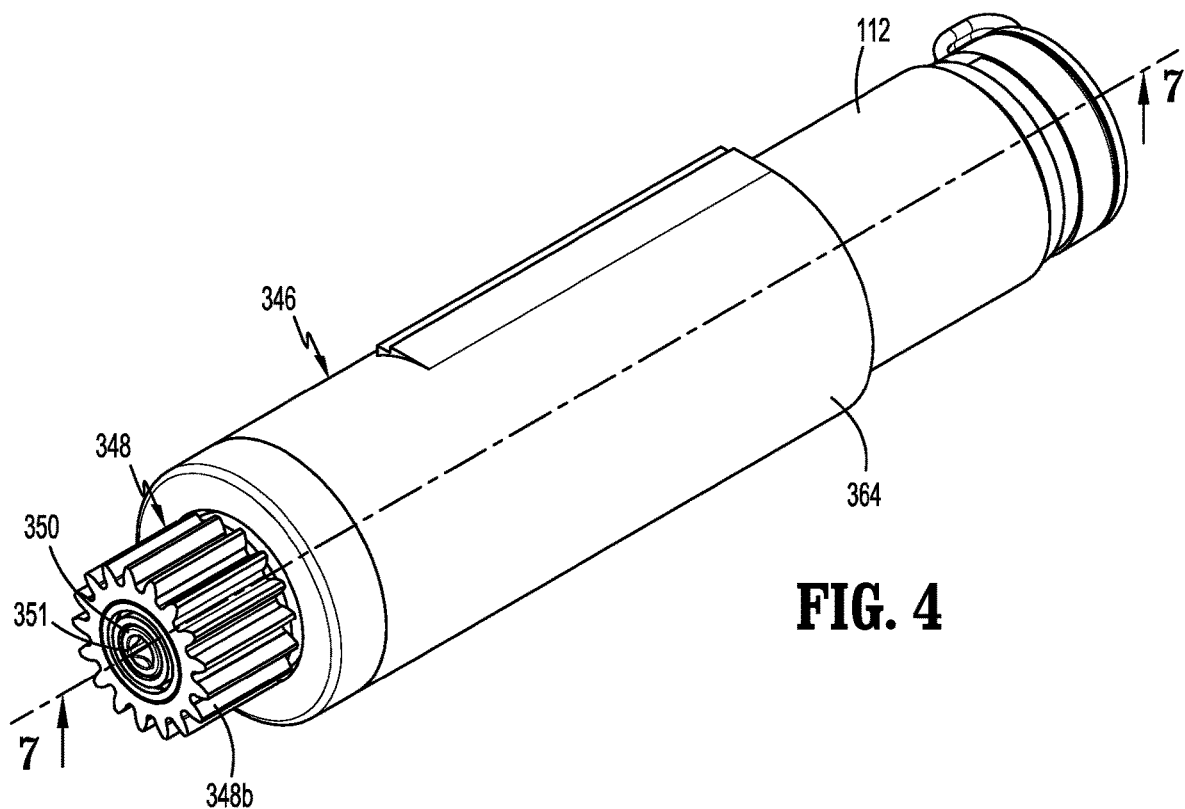
FIG. 4 is a perspective view illustrating a motor, an elongate ring gear, and outputs of the instrument module of FIG. 2A.
Figure 5:
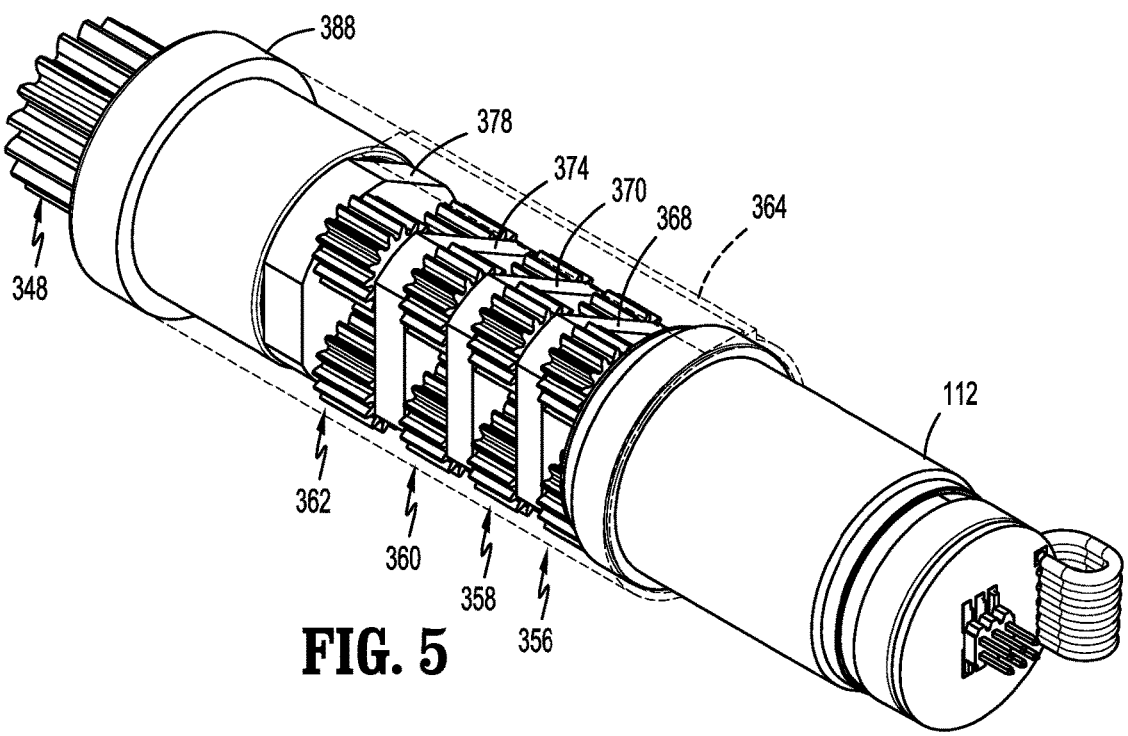
FIG. 5 is a perspective view, with the elongate ring gear shown in phantom, illustrating a plurality of planetary gear assemblies of the instrument module of FIG. 2A.
Figure 6:
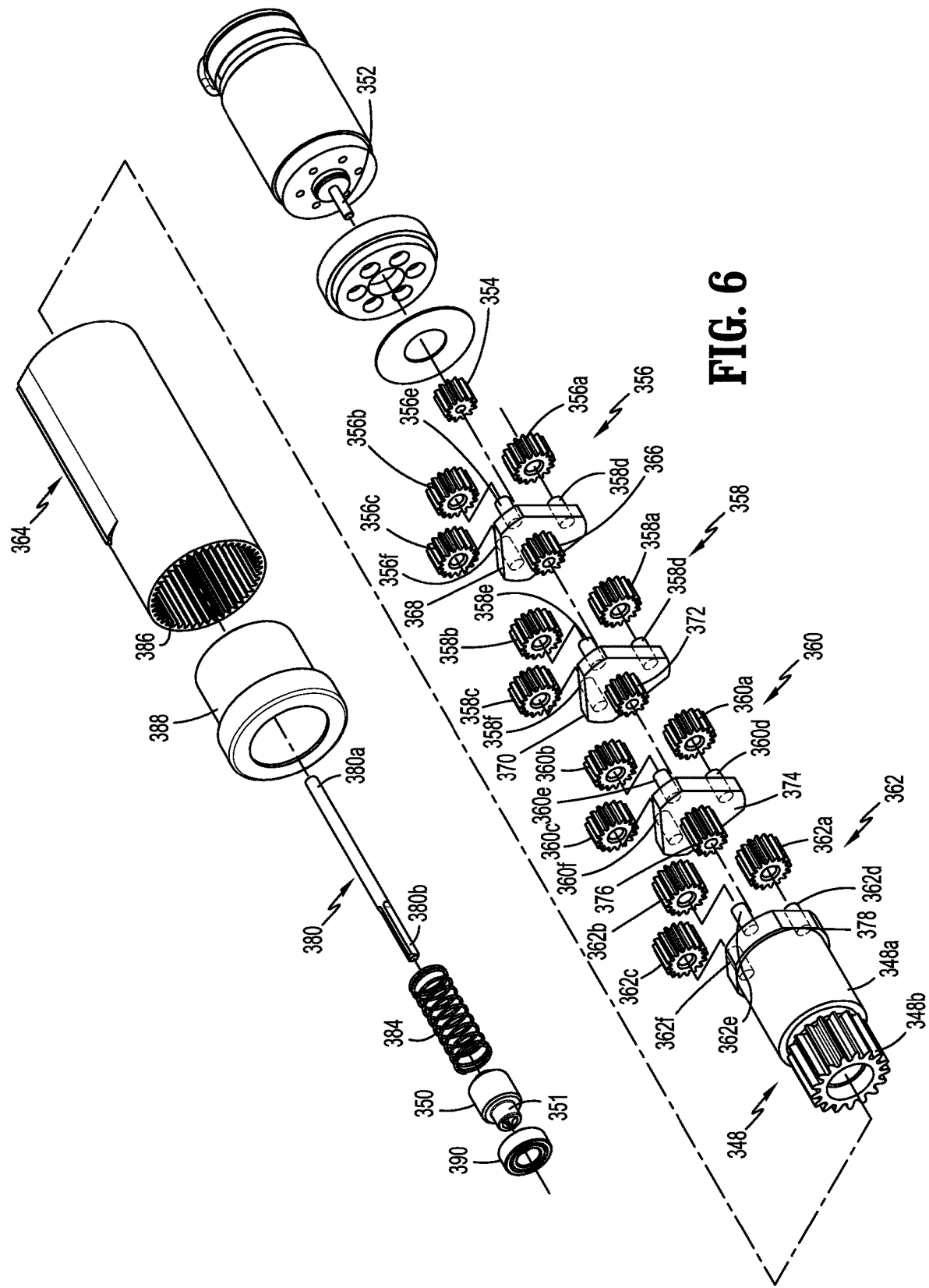
FIG. 6 is a perspective view, with parts separated, of the components shown in FIG. 5.
Figure 7:
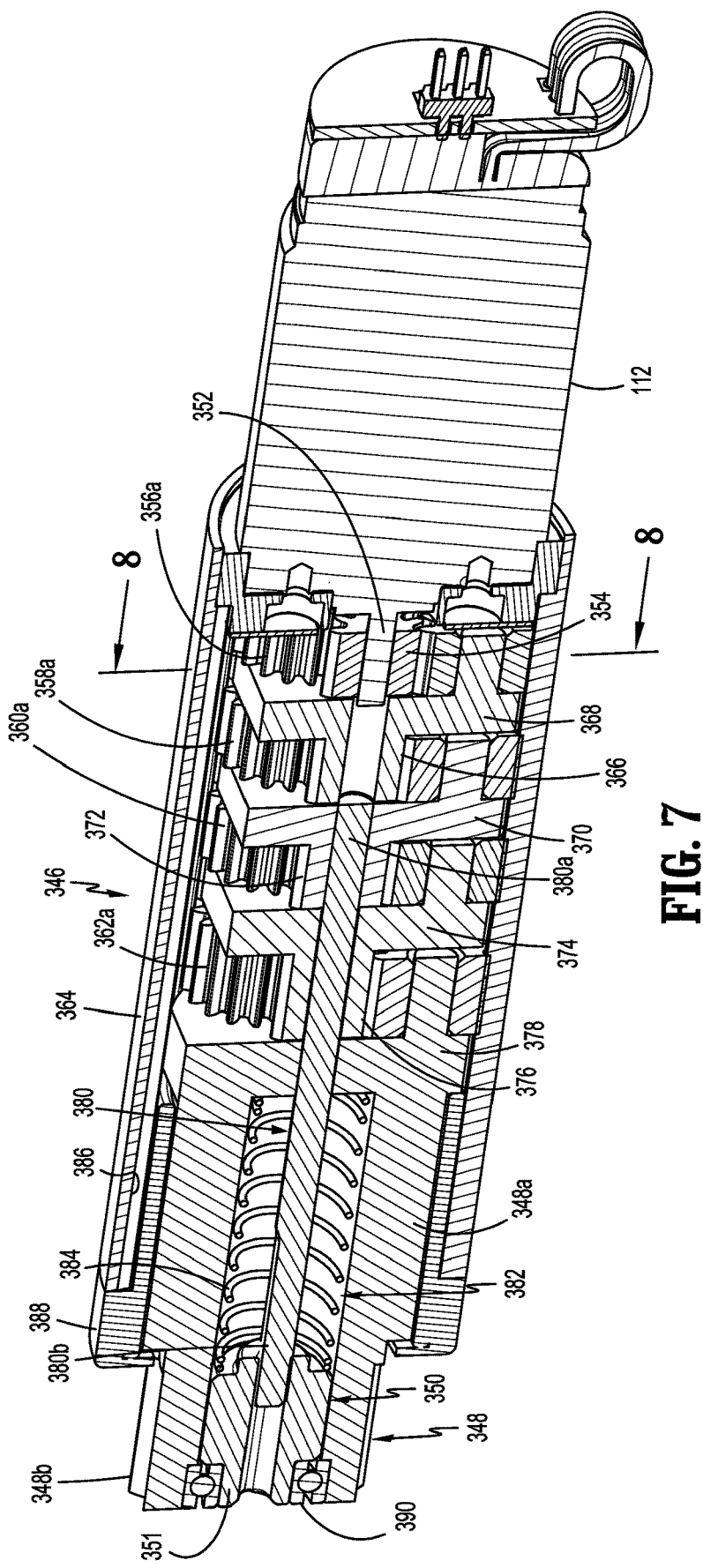
FIG. 7 is a cross-sectional view taken along line 7-7 in FIG. 4.
Figure 8:
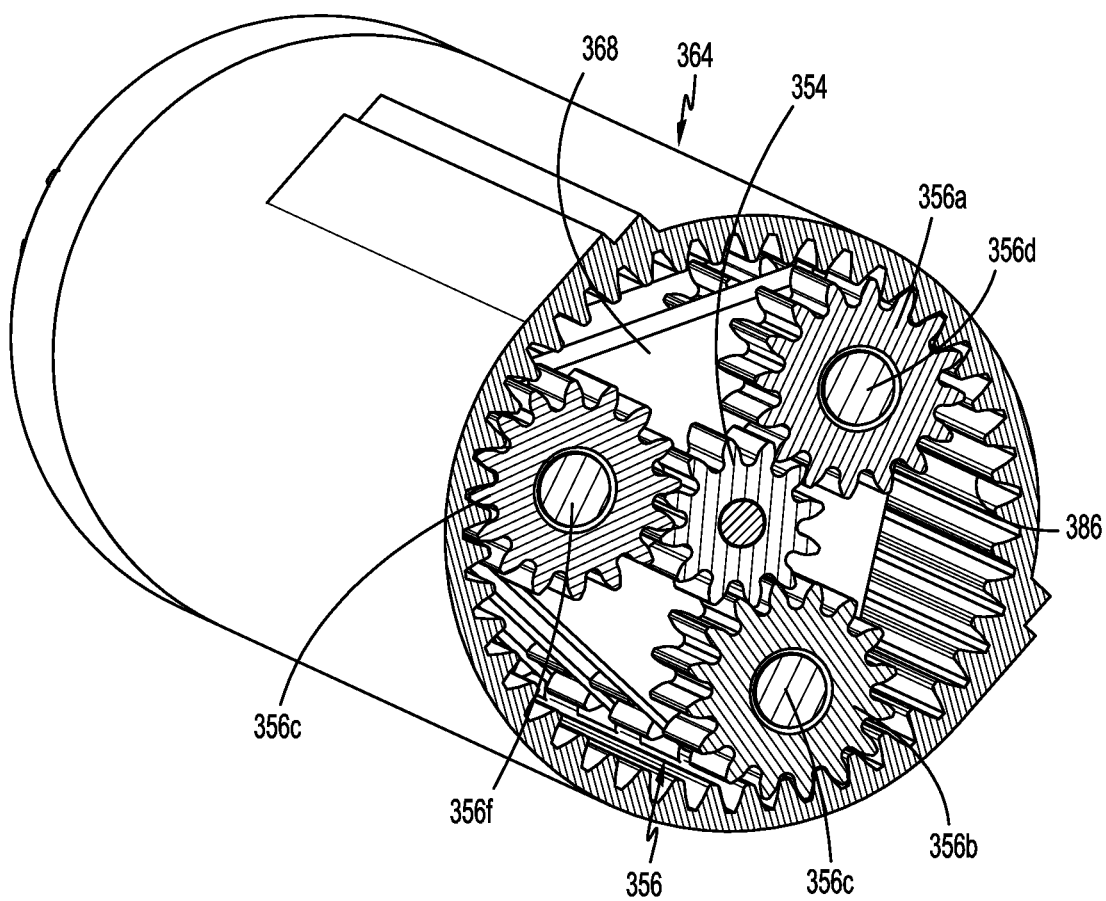
FIG. 8 is a cross-sectional view taken along line 8-8 in FIG. 7.

The instrument module 322 further includes a gearbox 346, such as, for example, a planetary gearbox, operably coupled to the drive motor 112, and first and second outputs 348, 350 (FIG. 4) drivingly coupled to the gearbox 346 and configured to rotate about a longitudinal axis defined by the gearbox 346. The gear box 346 is configured to transfer power from the motor 112 into a rotation of the first output 348 at a high-torque and low-speed, and a rotation of the second output 350 at a high-speed and low-torque. Rotation of the output 348 or output 350 by the motor 112 functions to drive shafts and/or gear components of the handle assembly 100 in order to perform an operation of a corresponding surgical loading unit, such as, for example, the surgical loading unit 200 (FIG. 17). For example, the motor 112 is configured move the jaw members 206, 208 of the end effector 204 relative to one another and to fire staples from the end effector 204.

With reference to FIGS. 4-8, further details of the various components of the instrument module 322 will now be described. The motor 112 has a rotatable motor shaft 352 (FIG. 6) to which a main sun gear 354 is non-rotatably fixed such that the main sun gear 354 rotates with the motor shaft 352 about a longitudinal axis defined by the motor shaft 352. The gear box 346 includes a plurality of planetary gear assemblies 356, 358, 360, 362 and an elongate ring gear 364 disposed about and operably coupled to the plurality of planetary gear assemblies 356, 358, 360, 362.

The first planetary gear assembly 356 is operably coupled to the main sun gear 354 such that the first planetary gear assembly 356 rotates about the longitudinal axis of the motor shaft 352 in response to a rotation of the main sun gear 354. The first planetary gear assembly 356 increases the torque output of the motor 112 while reducing the output rotational speed. The first planetary gear assembly 356 includes a first carrier 368, a first sun gear 366, and a plurality of planetary gears 356a, 356b, 356c. The first carrier 368 has a plurality (e.g., three) of pins 356d, 356e, 356f fixed thereto and extending proximally from a proximal side thereof. The first sun gear 366 is rotationally fixed to a distal side of the first carrier 368 and centrally aligned with the longitudinal axis of the motor shaft 352. The planetary gears 356a, 356b, 356c are rotatably coupled to the respective pins 356d, 356e, 356f of the first carrier 368. The planetary gears 356a, 356b, 356c are in meshing engagement with the main sun gear 354 to rotate in response to a rotation of the main sun gear 354. As will be described, the elongate ring gear 364 is rotationally fixed relative to the outer shell 328 (FIG. 2A) such that the first planetary gear assembly 356 rotates as a unit about the longitudinally axis of the motor shaft 352 in response to a rotation of the main sun gear 354.

The second planetary gear assembly 358 includes a second carrier 370, a second sun gear 372, and a plurality of planetary gears 358a, 358b, 358c. The second planetary gear assembly 358 has an increased torque output and reduced rotational speed output relative to the first planetary gear assembly 356. The second carrier 370 has a plurality (e.g., three) of pins 358*d*, 358*e*, 358*f* fixed thereto and extending proximally from a proximal side thereof. The second sun gear 372 is rotationally fixed to a distal side of the second carrier 370 and centrally aligned with the longitudinal axis of the motor shaft 352. The planetary gears 358*a*, 358*b*, 358*c* of the second planetary gear assembly 358 are rotatably coupled to the respective pins 358*d*, 358*e*, 358*f* of the second carrier 370. The planetary gears 358*a*, 358*b*, 358*c* are in meshing engagement with the first sun gear 366 of the first planetary gear assembly 356 and the fixed elongate ring gear 364 such that the second planetary gear assembly 358 rotates in response to a rotation of the first planetary gear assembly 356.

The third planetary gear assembly 360 includes a third carrier 374, a third sun gear 376, and a plurality of planetary gears 360*a*, 360*b*, 360*c*. The third planetary gear assembly 360 has an increased torque output and reduced rotational speed output relative to the second planetary gear assembly 358. The third carrier 374 has a plurality (e.g., three) of pins 360*d*, 360*e*, 360*f* fixed thereto and extending proximally from a proximal side thereof. The third sun gear 376 is rotationally fixed to a distal side of the third carrier 374 and centrally aligned with the longitudinal axis of the motor shaft 352. The planetary gears 360*a*, 360*b*, 360*c* of the third planetary gear assembly 360 are rotatably coupled to the respective pins 360*d*, 360*e*, 360*f* of the third carrier 374. The planetary gears 360*a*, 360*b*, 360*c* of the third planetary gear assembly 360 are in meshing engagement with the second sun gear 372 of the second planetary gear assembly 358 and the elongate ring gear 364 such that the third planetary gear assembly 360 rotates as a unit in response to a rotation of the second planetary gear assembly 358.

The fourth planetary gear assembly 362 includes a fourth carrier 378 and a plurality of planetary gears 362*a*, 362*b*, 362*c*. The fourth planetary gear assembly 362 has an increased torque output and reduced rotational speed output relative to the third planetary gear assembly 360. The fourth carrier 178 is connected to, monolithically formed with, or otherwise non-rotatably coupled to a proximal end of the first output 348 and has a plurality (e.g., three) of pins 362*d*, 362*e*, 362*f* fixed thereto and extending proximally from a proximal side thereof. The planetary gears 362*a*, 362*b*, 362*c* of the fourth planetary gear assembly 362 are rotatably coupled to the respective pins 362*d*, 362*e*, 362*f* of the fourth carrier 378. The planetary gears 362*a*, 362*b*, 362*c* of the fourth planetary gear assembly 362 are in meshing engagement with the third sun gear 376 of the third planetary gear assembly 360 and the elongate ring gear 364 such that the fourth planetary gear assembly 362 and the first output 348 rotate together in response to a rotation of the third planetary gear assembly 360. It is contemplated that the gear box 346 may include more or less than the four planetary gear assemblies and/or other types of gears.

With continued reference to FIGS. 4-8, the first output 348 is configured to generate a relatively high torque (e.g., about 625 oz-in) and a relatively low speed (e.g., 24 rpm) and includes a cylindrical body 348*a* received in a distal end portion of the elongate ring gear 364, and a gear 348*b*, such as, for example, a pinion gear formed with a distal end portion of the cylindrical body 348*a*. The pinion gear 348*b* of the first output 348 is configured to be selectively operably coupled to a driven member 209 (FIG. 17) of a first type of surgical end effector, such as, for example, surgical end effector 204 (FIG. 17) of the linear stapler 10.

The surgical instrument module 322 further includes a drive shaft 380 having a proximal end portion 380*a* non-rotatably coupled to the second planetary gear assembly 358 such that the drive shaft 380 is configured to rotate with the second planetary gear assembly 358. In particular, the proximal end portion 380*a* of the drive shaft 380 is received within and rotationally fixed to the second sun gear 372 of the second planetary gear assembly 358. The drive shaft 380 has a distal end portion 380*b* extending longitudinally through the third and fourth planetary gear assemblies 360, 362 while being freely rotatable therein. The distal end portion 380*b* of the drive shaft 380 may have a non-circular cross-sectional shape, such as, for example, a tri-lobe shape.

The second output 350 is attached to the distal end portion 380*b* of the drive shaft 380 and is configured to rotate with the drive shaft 380 about a longitudinal axis of the drive shaft 380. The second output 350 is configured to generate a relatively low torque (e.g., 25 oz-in) and a relatively high speed (e.g., 600 rpm) and includes a socket 351 that is configured to operably couple to a corresponding driven element (not explicitly shown) of a different type of surgical end effector than the first output 348. For example, the second output 350 of the surgical instrument module 322 may be configured to carry out functions of a surgical end effector of a hernia tacker (not shown) or a surgical end effector of a small-diameter vascular stapler (not shown).

The second output 350 is concentrically disposed within the first output 348 and is configured to rotate simultaneously with the first output 348 in response to an activation of the same motor, namely the motor 112. However, as noted above, the first and second outputs 348, 350 rotate at different speeds and with different torques from one another. The second output 350 is received in an elongate cavity 382 defined in the cylindrical body 348*a* of the first output 348. A biasing member 384 is disposed within the cavity 382 and captured between the second output 350 and an inner surface of the cylindrical body 348*a* of the first output 348. The biasing member 384 is configured to distally-bias the second output 350 into a position in which the second output 350 is concentric within the first output 348. The biasing member 384 ensures that even if the socket 351 of the second output 350 is out of radial alignment with the driven element of the end effector assembly that the socket 351 will engage the driven element as the second output 350 rotates the socket 351 into radial alignment with the driven element.

With continued reference to FIGS. 4-8, the elongate ring gear 364 of the gear box 346 encapsulates each of the planetary gear assemblies 356, 358, 360, 362 and is rotationally fixed relative to the outer shell 328 (FIG. 2A) and the motor 112. The elongate ring gear 364 has an annular inner surface defining a plurality of longitudinally-extending teeth 386 that are in meshing engagement with the planetary gears of each of the planetary gear assemblies 356, 358, 360, 362. A first bushing 388 may be provided to capture the first output 348 in the elongate ring gear 364 and a second bushing 390 may be provided to capture the second output 350 in the first output 348.

With brief reference to FIG. 3, the handle assembly 100 further includes a rack 126 located in the barrel portion 118 of the handle housing 110 and extends parallel with the barrel portion 118. The rack 126 is axially supported in the handle housing 110 has a distal end portion axially fixed to a firing rod 124 (FIG. 10) configured to operably couple to the drive assembly 209 (FIG. 17) of the end effector 204. The rack 126 is operably coupled to the output pinion gear 348 (FIGS. 3A and 3B). In aspects, the rack 126 may be directly engaged to the output pinion gear 348.

In operation, a surgical instrument is selected that is suitable for an operation to be performed. For example, the linear stapler 10 (FIG. 1) may be selected. The linear stapler 10 is typically used for stapling a type of tissue that is more suitable to receiving staples that are deployed with a high torque and at a low speed. The surgical instrument module 322 is inserted into the handle housing 110 of the linear stapler 10, whereby the pinion gear 348b of the first output 348 operably engages a driven element, such as rack 126 (FIG. 3) or a corresponding pinion gear of the handle assembly 100 of the linear stapler 10. In aspects, a preassembled, disposable, sterile, and/or funnel-shaped insertion guide may be implemented to assist in passing the surgical instrument module 322 into the handle housing 110. When the insertion guide is removed, the handle housing 110 remains sterile through this aseptic transfer procedure. With the instrument module 322 disposed within the handle housing 110, the door 120 is closed, thereby sealing the instrument module 322 in the sterile handle portion 108. Further, the card edge header 143 of the printed circuit board 182 of the handle assembly 100 is connected to the card edge connector 340 of the instrument module 322.

To operate a stapling function of the surgical end effector 204 of the linear stapler 10, the fire switch 106 (FIG. 1) may be toggled, whereby the battery 338 of the instrument module 322 provides power to the motor 112, which drives a rotation, in turn, of the first, second, third, and fourth planetary gear assemblies 356, 358, 360, 362. The planetary gear assemblies 356, 358, 360, 362 consecutively enhance the torque and reduce the speed output by the pinion gear 348b of the first output 348 compared to the torque and speed originating from the motor 112. The high-torque, low-speed output by the first output 348 results translates the rack 126 (FIG. 3) along the longitudinal axis of the barrel portion 118 of the handle housing 110. Since the rack 126 is operably coupled to the drive assembly 209 of the surgical end effector 204 via the firing rod 124 (FIG. 1), translation of the rack 126 results in one of an opening or closing of the jaw members 206, 208 depending on the direction of translation of the rack 126. To fire staples from the surgical end effector 200, the safety switch 116 (FIG. 1) is actuated, and then the bottom button 122b of the fire switch 122 is actuated, whereby the sled 213 (FIG. 17) of the surgical end effector 204 translates through the cartridge assembly 208 to fire the staples into tissue with a high force and at a low speed.

If a different surgical procedure is to be performed, for example, a hernia repair procedure, a hernia tacker may be selected for use rather than the linear stapler 10 while still enabling utilization of the same surgical instrument module 322. To properly treat tissue, a hernia tacker demands less torque but a higher actuation speed than the linear stapler 10. The instrument module 322 is inserted into a handle portion of a hernia tacker, whereby the socket 351 of the second output 350 engages a driven element (e.g., a rod) of the hernia tacker. To operate the hernia tacker, an actuation of a switch or toggle activates the battery 338 of the instrument module 322, thereby providing power to the motor 112, which drives a rotation, in turn, of the first and second planetary gear assemblies 356, 358. Since the drive shaft 380 is fixed to the second sun gear 372 of the second planetary gear assembly 358, the drive shaft 180 rotates with the rotation of the second planetary gear assembly 358. The second output 350, which is non-rotatably attached to the distal end portion 380b of the drive shaft 380, rotates with the drive shaft 380 to effect a function of the hernia tacker, such as a deployment of a surgical tack into tissue at a low torque and a high speed.

It is contemplated that each of the first and second drive outputs 348, 350 may be simultaneously coupled to two distinct driven elements of a particular surgical instrument to perform discrete functions of the surgical instrument.

With reference to FIGS. 1 and 9-17, the shaft assembly 102 of the surgical instrument 10 generally includes the knob housing 104, the shaft portion 106, which has a proximal end portion 106a received within and non-rotationally coupled to the knob housing 104, and an articulation switch 128, such as, for example, a manual articulation lever coupled to an upper housing half of the knob housing 104. The knob housing 104 is supported between the barrel portion 118 and the proximal end portion 106a of shaft portion 106. The knob housing 104 is rotatably coupled to the handle housing 110 such that a manual rotation of the knob housing 104 results in a corresponding rotation of the surgical loading unit 200 (e.g., the surgical loading unit 200 rotates about a central longitudinal axis "X" defined by the shaft portion 106).

The articulation switch or lever 128 has a stem 130 protruding downwardly therefrom, which is received in a corresponding aperture 132 defined in the upper housing half of the knob housing 104. The articulation lever 128 is configured to actuate an articulation of the end effector 204 (e.g., move the end effector 204 along a horizontal plane between a position coaxial with the shaft portion 106 and multiple positions out of parallel alignment with the shaft portion 106), as will be described herein.

With reference to FIGS. 9-13, the shaft assembly 102 further includes a plurality of mechanical components responsible for converting the manual rotation of the articulation lever 128 into the articulation of the end effector 204 (FIG. 17). In particular, the shaft assembly 102 includes a cam plate 134 coupled to the articulation lever 128 and an articulation link 136 coupled to the cam plate 134 and the surgical loading unit 200 when the surgical loading unit 200 is coupled to the shaft portion 106. The cam plate 134 is received within the knob housing 104 and is non-rotationally coupled to the articulation lever 128. For example, the stem 130 of the articulation lever 138 may be fixed to the cam plate 134 via fasteners such that rotation of the articulation lever 128 about a pivot axis "Y" (FIG. 13) results in a rotation of the cam plate 134.

The cam plate 134 has an annular outer periphery having a plurality of gear teeth or ridges 138. A pawl 140 may be provided within the knob housing 104 and may be resiliently biased by a pawl spring 142 into engagement with the teeth 138 of the cam plate 134 to resist, without preventing, rotation of the cam plate 134. In this way, an articulation orientation of the end effector 204, as set by the radial orientation of the articulation lever 128 relative to the knob housing 104, is maintained by the engagement of the pawl 140 with the teeth 138 of the cam plate 134.

The articulation link 136 has a proximal end portion 136a received within the knob housing 104 and a distal end portion 136b extending through the shaft portion 106 for selective engagement with a hooked proximal end portion 215 (FIG. 17) of an articulation shaft 217 of the surgical loading unit 200. The proximal end portion 136a of the articulation link 136 may be an elongated plate disposed below the cam plate 134, and the distal end portion 136b of the articulation link 136 may be a shaft or bar fixed to and extending distally from the elongated plate 136a. A cam pin 144 is fixed to the proximal end portion 136a of the articulation link 136 and protrudes upwardly therefrom and into an arcuate cam slot 146 defined in the cam plate 134. The cam slot 146 is configured to drive a translation of the cam pin 144 as the cam plate 134 rotates in either of a clockwise or counter-clockwise direction. The distal end portion 136b of the articulation link 136 has a hooked distal end 136c configured to operably couple to the hooked proximal end 215 (FIG. 17) of the articulation shaft 217 of the surgical loading unit 200 such that the translation of the articulation link 136 results in an articulation of the end effector 204 relative to the proximal body portion 202 of the surgical loading unit 200.

With continued reference to FIGS. 9-13, the shaft assembly 102 further includes a plurality of operably connected mechanical and electrical components responsible for preventing an actuation of articulation lever 128 or an activation of the motor 112 unless the surgical loading unit 200 is properly assembled/loaded to the shaft assembly 102. In particular, the shaft assembly 102 includes a slider 150, such as, for example, an elongate body supported in the knob housing 104 and configured to translate within and relative to the knob housing 104 between a proximal position and a distal position. The slider 150 may be rectangular, tubular, cylindrical, block-shaped, or assume any other suitable shape. The slider 150 is keyed to an internal surface of the knob housing 104 to prevent relative rotation between the slider 150 and the knob housing 104. The slider 150 defines a longitudinally-extending passageway 152 (FIG. 13) through which the firing rod 124 extends.

The slider 150 has a tab 154, such as, for example, a fin protruding upwardly from a proximal end portion 150a thereof. In aspects, the tab 154 may be any suitable surface feature, such as, for example, a ridge, a tooth, or the like. The tab 154 of the slider 150 is configured for removable receipt in a correspondingly-shaped notch 156 defined in the cam plate 134. In aspects, the notch 156 may be elongated and extend radially inward from the outer periphery of the cam plate 134. The notch 156 is configured to be parallel with the longitudinal axis "X" of the shaft portion 106 when the articulation lever 128 is parallel with the longitudinal axis "X" of the shaft portion 106 (e.g., when the articulation lever 128 is in a non-articulated orientation). A biasing member 158, such as, for example, a coil spring, may be provided to bias the slider 150 in the distal position, in which the tab 154 is received in the notch 156 of the cam plate 134 to prevent rotation of the articulation lever 128. In aspects, the cam plate 134 may have a tab whereas the slider 150 may have a corresponding notch.

With reference to FIGS. 11, 13, 15, and 16, the shaft assembly 102 further includes a tubular shaft 160 and a coupling assembly 162 attached to a distal end portion 160b of the tubular shaft 160. The tubular shaft 160 extends through the shaft portion 106 and is disposed about the firing rod 124. The tubular shaft 160 has a proximal end portion 160a extending into the knob housing 104 and into abutment with a distal end portion 150b of the slider 150. In aspects, the proximal end portion 160a of the tubular shaft 160 may be fixed to or otherwise coupled to the distal end portion 150b of the slider 150 so that proximal or distal translation of the tubular shaft 160 results in a corresponding translation of the slider 150.

Figure 15:
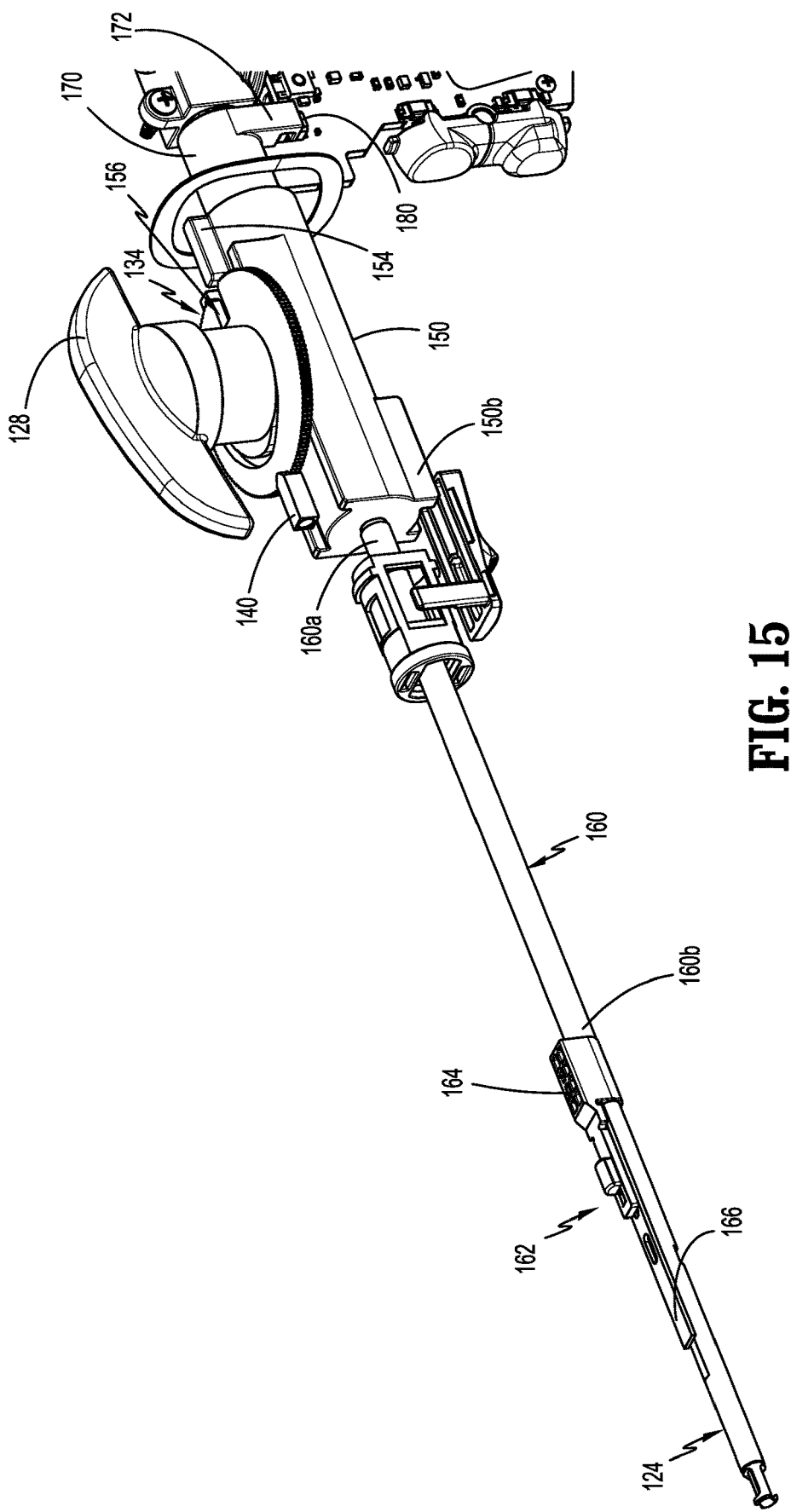
FIG. 15 is a side perspective view illustrating internal components of the handle assembly and shaft assembly of FIG. 1.
Figure 16:
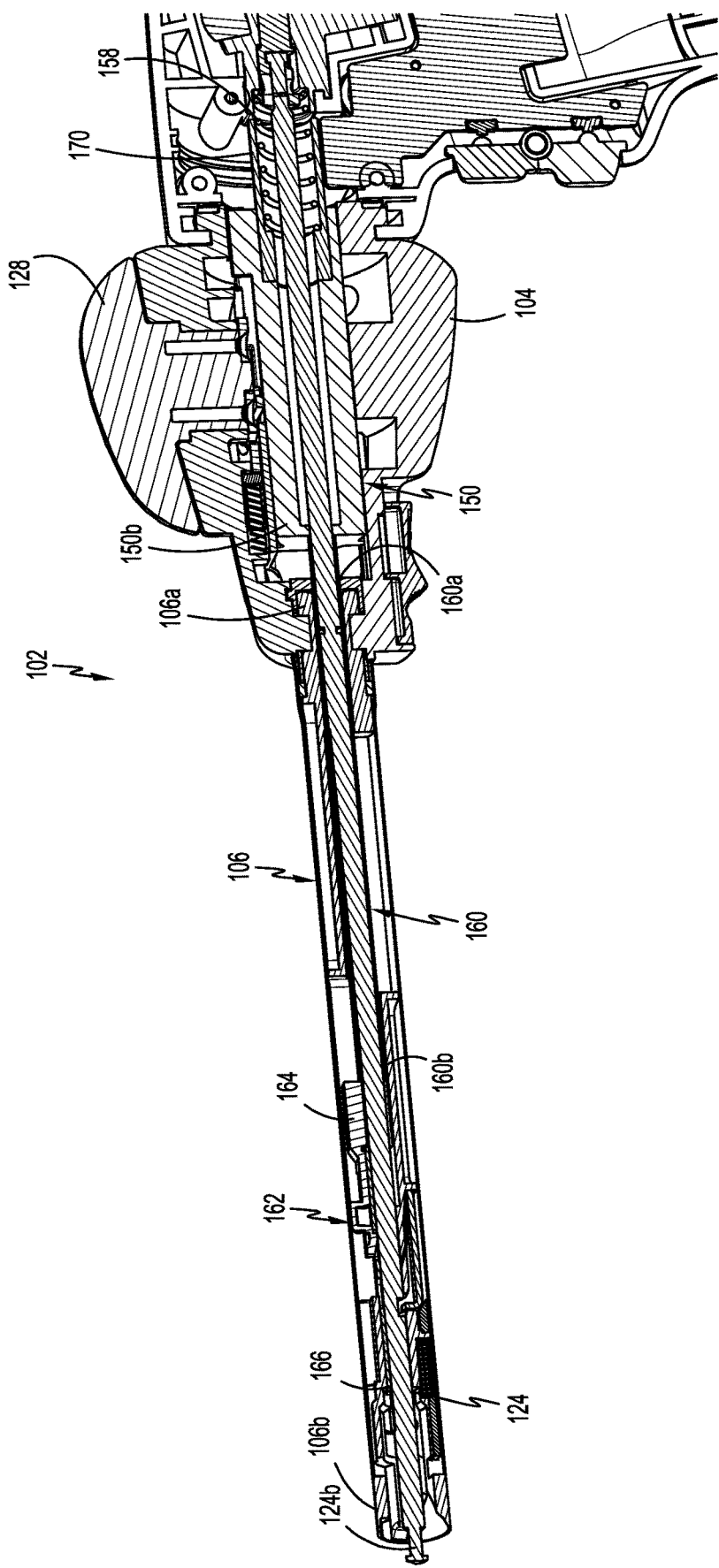
FIG. 16 is a longitudinal cross-sectional view of the surgical instrument of FIG. 1.

The coupling assembly 162, as best shown in FIGS. 15 and 16, is fixed to the distal end portion 160b of the tubular shaft 160 and is disposed adjacent a distal end portion 106b of the shaft portion 106. The coupling assembly 162 includes a proximal link 164 fixed to the tubular shaft 106 and a distal link 166 fixed to the proximal link 164. The distal link 166 is configured to be engaged to the proximal body portion 202 (FIG. 17) of the surgical loading unit 200 such that the tubular shaft 160 and the slider 150 translate proximally from the distal position to the proximal position upon receipt of the surgical loading unit 200 in the distal end portion 106b of the shaft portion 106.

With reference to FIGS. 13-16, the shaft assembly 102 further includes a tubular member 170 fixed within the proximal end portion 150a of slider 150 and projecting proximally therefrom. The biasing member 158 may be received within the tubular member 170 to distally bias the slider 150. The tubular member 170 has a flag 172 extending laterally outward therefrom and received within the handle housing 110. The flag 172 is configured to move with the slider 150 as the slider 150 translates between the proximal and distal positions. In aspects, the flag 172 may be monolithically formed with or otherwise coupled directly to the slider 150.

The handle assembly 100 further includes a sensor 180 fixed to the printed circuit board 182 and disposed adjacent the flag 172. The sensor 180 may be in communication with the motor 112 (FIG. 1), either directly or via a processor 184 (FIG. 14), and configured to sense an axial position of the flag 172. For example, the sensor 180 may be a photointerrupter fixed within the handle assembly 100, and the flag 172 may be configured to block a signal of the photointerrupter 180 when the slider 150 is in the proximal position. In aspects, the sensor 180 may be any suitable type of position sensor, such as, for example, a hall effect sensor, an electro-optical sensor, photoelectric sensor, or the like.

The sensor 180 may be configured to prevent operation of the motor 112 when the sensor 180 senses that the slider 150 is in the distal position, which is indicative of an absence of a properly loaded surgical loading unit 200 to the shaft assembly 102 and/or permit operation of the motor 112 when the sensor 180 senses that the slider 150 is in the proximal position, which is indicative of a surgical loading unit 200 being properly loaded to the shaft assembly 102. In aspects, the processor 184 may be programmed to inhibit power from being delivered to the motor 112 upon the sensor 180 sensing that the flag 172 is in the distal position or failing to sense that the flag 172 is in the proximal position. In aspects, the processor 184 may be programmed to permit power to be delivered to the motor 112 upon the sensor 180 sensing that the flag 172 is in the proximal position or failing to sense that the flag is in the distal position. In other aspects, the sensor 180 may be in communication with a display or speaker for providing a visual or audible indication that the surgical loading unit 200 is not properly inserted.

In aspects, the sensor 180 may be configured to enable the software control to know that a SULU is present. The flag 172 engages the photo interrupter or sensor 180, acting as a switch and electrically notifying the device that a SULU is present. When all other safety conditions are met, such as the device is fully clamped, the green safety switch is enabled, allowing the green safety to change states if depressed. Once depressed, the LED indicator may transition from blinking to illuminating a solid green light. With the solid green indicator, fire mode is enabled and the surgical instrument 10 may be actuated when ready.

With reference to FIGS. 17-19, the surgical loading unit 200 includes the proximal body portion 202 and the end effector 204. The proximal body portion 202 is releasably attached to the distal end portion 106b of the shaft portion 106, and the end effector 204 is pivotally attached to a distal end of the proximal body portion 202 of the end effector 200. The end effector 204 is configured to articulate relative to the proximal body portion 202 via a manual rotation of articulation lever 128. The end effector 204 includes an anvil assembly 206 and a cartridge assembly 208. The cartridge assembly 208 is pivotal in relation to the anvil assembly 206 and is movable between an open or unclamped position and a closed or clamped position for insertion through a cannula of a trocar.

To assemble the surgical loading unit 200 to the surgical instrument 10, the proximal body portion 202 of the surgical loading unit 200 is axially inserted within the distal end portion 106b of the shaft portion 106 and rotated relative to the shaft portion 106 to lockingly engage a pair of bosses 224a, 224b (FIG. 17) of the surgical loading unit 200 within a corresponding pair of recesses defined within shaft portion 106. Upon axially inserting the surgical loading unit 200 into shaft portion 106, proximal body portion 202 engages the coupling assembly 162 (FIGS. 15 and 16) to proximally translate the tubular shaft 160 and the attached slider 150 against the distally-oriented bias of the biasing member 158. As the slider 150 is moved from the distal position to the proximal position, the tab 154 of the slider 150 is displaced out of the notch 156 in the cam plate 134 to allow for a manual rotation of the articulation lever 128. Prior to loading the surgical loading unit 200, the tab 154 of the slider 150 is received within the notch 156 of the cam plate 134 preventing an inadvertent rotation of the articulation lever 128, which could damage components of the surgical instrument 10 and/or result in the improper loading of the surgical loading unit 200.

Figure 9:
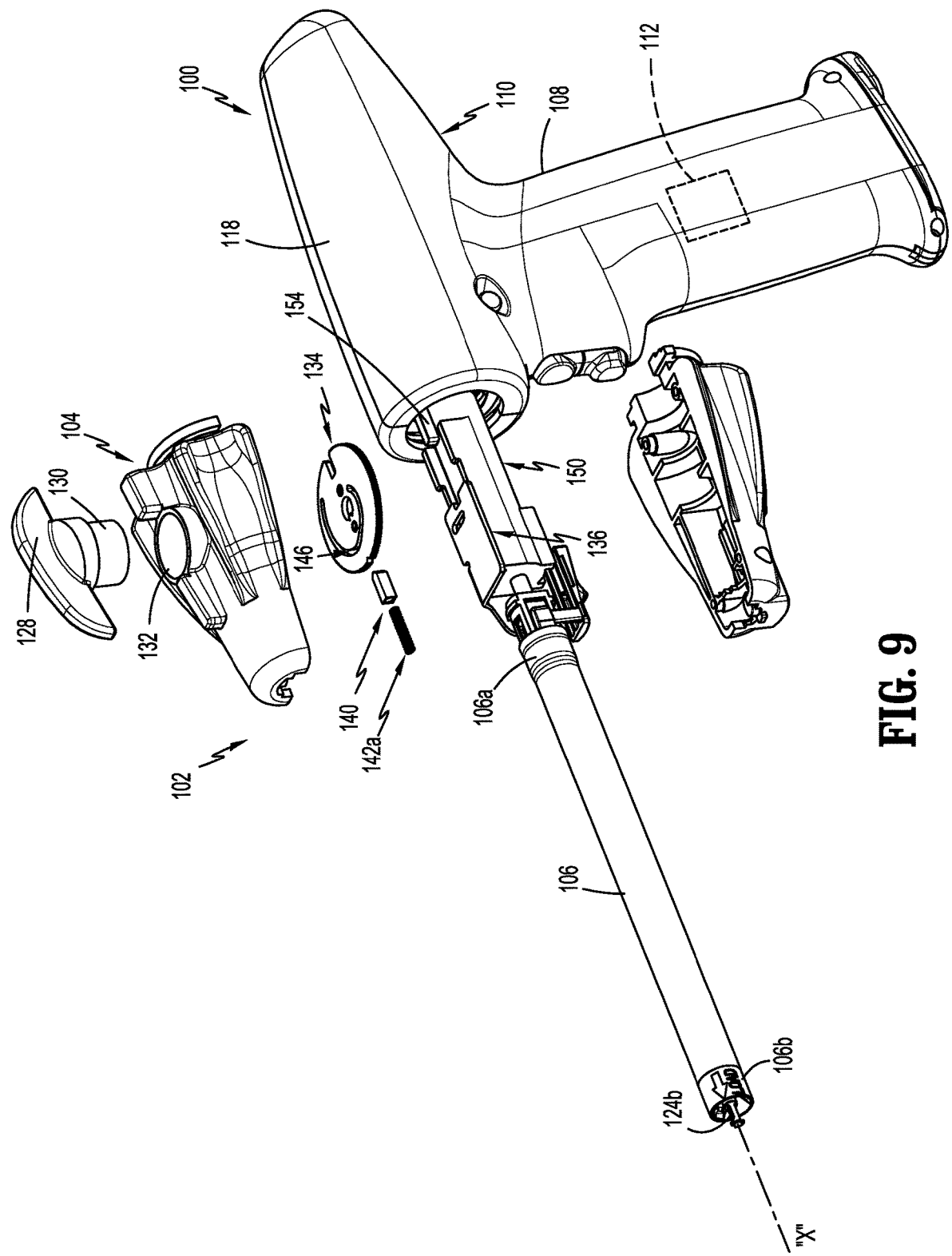
FIG. 9 is a side perspective view, with parts separated, illustrating components of the shaft assembly of FIG. 1 responsible for effecting articulation of an end effector.
Figure 12:
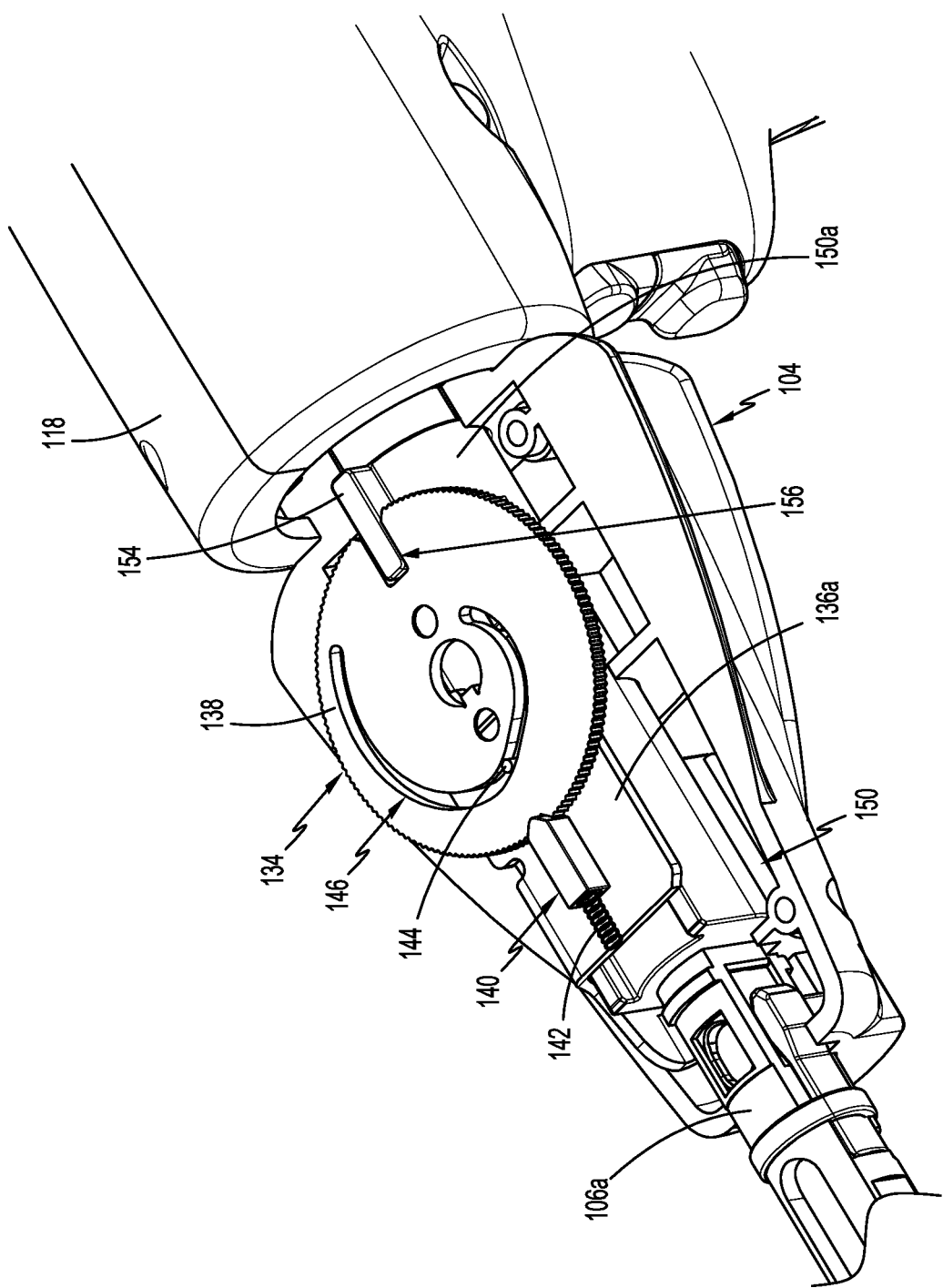
FIG. 12 is an elevational view illustrating internal components of a knob housing of the shaft assembly of FIG. 1.
Figure 13:
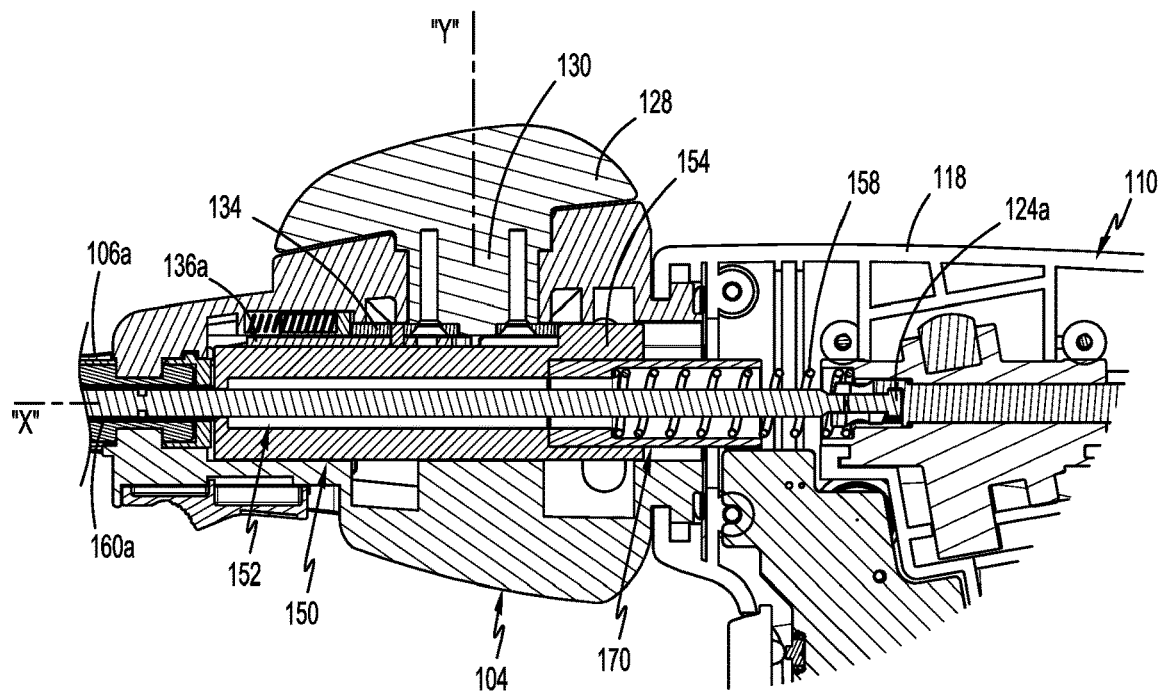
FIG. 13 is an enlarged longitudinal cross-sectional view illustrating a proximal end portion of the shaft assembly of FIG. 9 and a distal end portion of the handle assembly of FIG. 1.
Figure 14:
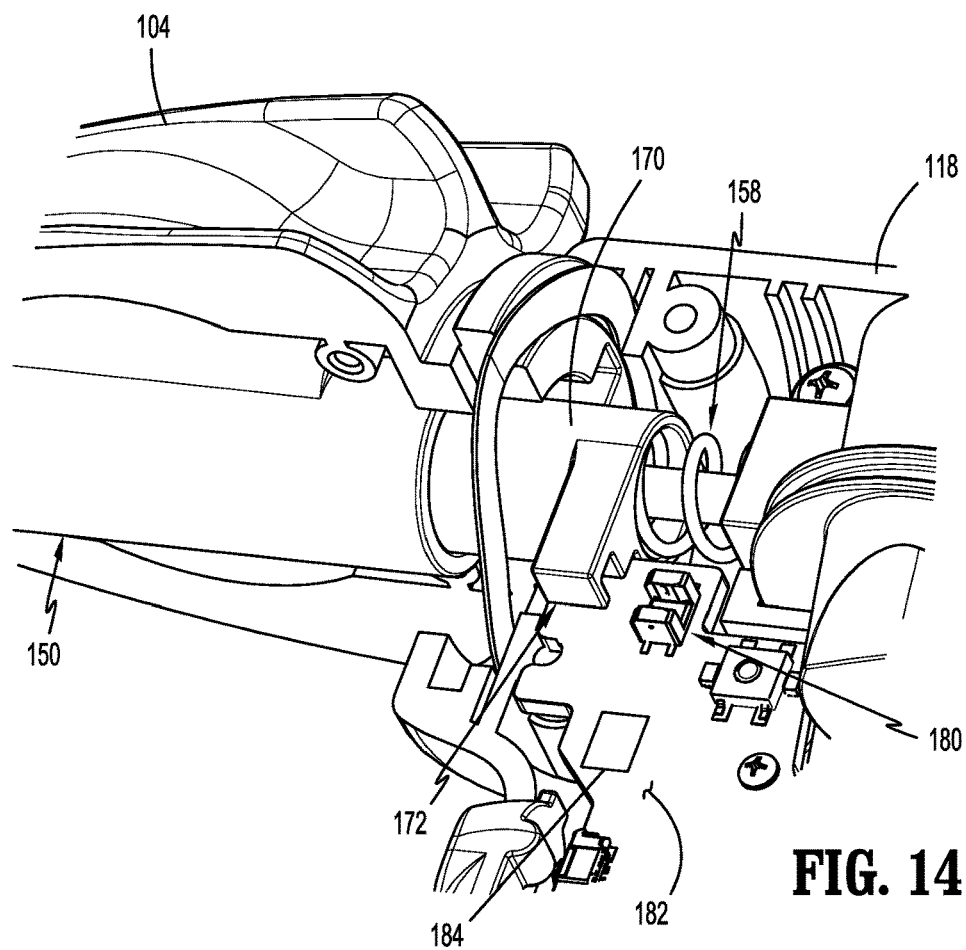
FIG. 14 is an enlarged perspective view illustrating a sensor and a flag of the surgical instrument of FIG. 1.

With reference to FIGS. 9, 12, and 13, to articulate the end effector 204 relative to the proximal body portion 202, a clinician may rotate the articulation lever 128, which in turn rotates the cam plate 134 to drive one of a distal or proximal translation of the articulation link 136 due to cam slot 146 of the cam plate 134 acting on the cam pin 144 of the articulation link 136. A translation of the articulation link causes a concomitant translation of the articulation shaft 217 of the surgical loading unit 200, whereby the end effector 204 is caused to articulate relative to the proximal body portion 202 either toward the left or the right (from the perspective of the user).

With reference to FIGS. 18 and 19, in aspects, a plurality of surgical loading units may be provided with each having a different length (e.g., 30 mm, 45 mm and 60 mm). There are multiple methods for the power assembly to determine the firing length, thereby determining when to begin retraction. One method is to install a one-wire ID chip 220 on the proximal end of the proximal body portion 202 configured to mate with a corresponding electrical contact (not explicitly shown) disposed within the distal end portion 106b of shaft portion 106 for communicating information about the surgical loading unit 200 to the processor 184 (FIG. 14) of the handle assembly 100. The chip 220 may have a unique identifier that will provide the handle assembly 100 with electronic information as to the reload length and required number of firing turns which in turn can be programmed into the software.

Another method is to use an algorithm that monitors the amount of motor current used to detect when the I-beam 211 of the surgical loading unit 200 has advanced to the point of colliding with the end of the anvil 206 slot. This contact will form a current spike that can be measured in software indicating the end-stop has been reached. The algorithm can be finely tuned to minimize the amount of force and articulation hinge deflection required to make this detection.

Another method integrates a sensor (not explicitly shown) inside the handle assembly 100. The sensor may, for example, measure motor torque and correlate the motor toque to the I-beam force or include a strain gauge to measure the module reaction torque. Both of these methods could effectively determine when the I-beam 211 end stop has been reached as a load spike will form when the I-beam 211 makes contact with the end of the anvil 206 slot.

Any of the components described herein may be fabricated from either metals, plastics, resins, composites or the like taking into consideration strength, durability, wearability, weight, resistance to corrosion, ease of manufacturing, cost of manufacturing, and the like.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A hand-held surgical instrument, comprising:
    a handle assembly;
    a shaft portion having a proximal end portion and a distal end portion;
    a knob housing coupled between the proximal end portion of the shaft portion and the handle assembly;
    an articulation lever rotationally coupled to the knob housing;
    a cam plate non-rotationally coupled to the articulation lever and disposed within the knob housing, the cam plate defining a notch therein;
    a slider supported in the knob housing and configured to translate within and relative to the knob housing between a proximal position and a distal position, the slider having a tab configured for receipt in the notch of the cam plate when the slider is in the distal position to prevent rotation of the cam plate; and
    a surgical loading unit having a proximal body portion configured to detachably couple to the distal end portion of the shaft portion, and an end effector pivotably coupled to the proximal body portion, the cam plate being configured to operably couple to the end effector such that the end effector articulates relative to the proximal body portion in response to a rotation of the cam plate, wherein the surgical loading unit is configured to move the slider toward the proximal position upon assembling the surgical loading unit to the distal end portion of the shaft portion.

2. The hand-held surgical instrument according to claim 1, further comprising:
    a flag attached to the slider and configured to move with the slider between the proximal and distal positions; and
    a sensor disposed adjacent the flag and configured to sense whether the slider is in the proximal position or the distal position.

3. The hand-held surgical instrument according to claim 2, wherein the sensor is a photointerrupter fixed within the handle assembly, and the flag is configured to block a signal of the photointerrupter when the slider is in the proximal position.

4. The hand-held surgical instrument according to claim 2, further comprising a motor configured to actuate a function of the end effector, wherein the sensor is in communication with the motor and configured to at least one of:

prevent operation of the motor when the sensor senses that the slider is in the distal position; or permit operation of the motor when the sensor senses that the slider is in the proximal position.

5. The hand-held surgical instrument according to claim 1, wherein the slider is an elongate body resiliently biased toward the distal position.

6. The hand-held surgical instrument according to claim 1, further comprising an articulation link extending through the shaft portion and including:
   a proximal end portion having a cam pin, the cam plate defining a cam slot in which the cam pin is received; and
   a distal end portion configured to operably couple to the end effector, wherein the articulation link is configured to translate in response to a rotation of the cam plate to articulate the end effector relative to the proximal body portion.

7. The hand-held surgical instrument according to claim 1, further comprising a pawl received in the knob housing, wherein the cam plate has a plurality of teeth extending from an outer periphery of the cam plate, the pawl engaged to the plurality of teeth to maintain a radial orientation of the cam plate.

8. The hand-held surgical instrument according to claim 1, wherein the shaft portion is configured to rotate about a longitudinal axis defined by the shaft portion in response to a manual rotation of the knob housing.

9. The hand-held surgical instrument according to claim 1, further comprising a firing rod extending longitudinally through a longitudinal passageway defined through the slider, the firing rod having a distal end portion configured to detachably couple to the surgical loading unit and configured to translate through the shaft portion to actuate a function of the end effector.

10. A hand-held surgical instrument, comprising:
    a handle housing;
    a shaft portion extending distally relative to the handle housing;
    a knob housing disposed between a proximal end portion of the shaft portion and the handle housing;
    an elongate body supported in the knob housing and configured to translate from a distal position to a proximal position in response to an insertion of a surgical loading unit into a distal end portion of the shaft portion, the elongate body having a tab;
    a cam plate configured to convert rotational motion into an articulation of an end effector of the surgical loading unit, wherein the cam plate defines a notch therein configured for receipt of the tab of the elongate body when the elongate body is in the distal position to prevent rotation of the cam plate;
    a flag attached to the elongate body and configured to move with the elongate body as the elongate body translates between the proximal and distal positions; and
    a sensor disposed adjacent the flag and configured to sense whether the elongate body is in the proximal position, thereby indicating the surgical loading unit is assembled to the hand-held surgical instrument.

11. The hand-held surgical instrument according to claim 10, further comprising the surgical loading unit, the surgical loading unit including:
    a proximal body portion configured to detachably couple to the distal end portion of the shaft portion; and
    the end effector pivotably coupled to the proximal body portion, the cam plate being configured to operably couple to the end effector such that the end effector articulates relative to the proximal body portion in response to a rotation of the cam plate.

12. The hand-held surgical instrument according to claim 10, wherein the sensor is a photointerrupter, and the flag is configured to block a signal of the photointerrupter when the elongate body is in the proximal position.

13. The hand-held surgical instrument according to claim 10, further comprising a motor configured to actuate a function of the surgical loading unit, wherein the sensor is in communication with the motor and configured to permit operation of the motor when the sensor senses that the elongate body is in the proximal position.

14. The hand-held surgical instrument according to claim 10, wherein the elongate body is resiliently biased toward the distal position.

15. The hand-held surgical instrument according to claim 10, wherein the shaft portion is configured to rotate about a longitudinal axis defined by the shaft portion in response to a manual rotation of the knob housing.

16. The hand-held surgical instrument according to claim 10, further comprising a firing rod extending longitudinally through a longitudinal passageway defined through the elongate body, the firing rod having a distal end portion configured to detachably couple to the surgical loading unit and configured to translate through the shaft portion to actuate a function of the surgical loading unit.

17. The hand-held surgical instrument according to claim 16, further comprising a tubular shaft disposed about the firing rod and having a proximal end portion engaged to the elongate body, and a distal end portion configured to be engaged by the surgical loading unit such that the tubular shaft translates the elongate body from the distal position to the proximal position upon receipt of the surgical loading unit in the distal end portion of the shaft portion.

18. A hand-held surgical instrument, comprising:
    a handle housing;
    a shaft portion extending distally relative to the handle housing;
    a knob housing disposed between a proximal end portion of the shaft portion and the handle housing;
    an elongate body supported in the knob housing and configured to translate from a distal position to a proximal position in response to an insertion of a surgical loading unit into a distal end portion of the shaft portion, the elongate body having a tab;
    a cam plate configured to convert rotational motion into an articulation of an end effector of the surgical loading unit, wherein the cam plate defines a notch therein configured for receipt of the tab of the elongate body when the elongate body is in the distal position to prevent rotation of the cam plate;
    an articulation lever rotationally coupled to the knob housing and non-rotationally coupled to the cam plate; and
    an articulation link including:
      a proximal end portion having a cam pin, the cam plate defining a cam slot in which the cam pin is received; and
      a distal end portion configured to operably couple to the surgical loading unit, wherein the articulation link is configured to translate in response to a rotation of the cam plate by the articulation lever.

19. A hand-held surgical instrument, comprising:
    a handle housing;
    a shaft portion extending distally relative to the handle housing;

a knob housing disposed between a proximal end portion of the shaft portion and the handle housing;

an elongate body supported in the knob housing and configured to translate from a distal position to a proximal position in response to an insertion of a surgical loading unit into a distal end portion of the shaft portion, the elongate body having a tab; and a cam plate configured to convert rotational motion into an articulation of an end effector of the surgical loading unit, wherein the cam plate defines a notch therein configured for receipt of the tab of the elongate body when the elongate body is in the distal position to prevent rotation of the cam plate; and a pawl received in the knob housing, wherein the cam plate has a plurality of teeth extending from an outer periphery of the cam plate, the pawl engaged to the plurality of teeth to maintain a radial orientation of the cam plate.

\* \* \* \* \*